US006911525B2

(12) United States Patent
Hill et al.

(10) Patent No.: US 6,911,525 B2
(45) Date of Patent: Jun. 28, 2005

(54) LIPOPEPTIDES AS ANTIBACTERIAL AGENTS

(75) Inventors: Jason Hill, Auburndale, MA (US); Ian Parr, Medford, MA (US); Michael Morytko, Framingham, MA (US); Jim Siedlecki, Burlington, MA (US); Xian Yang Yu, Billerica, MA (US); Jared Silverman, Brookline, MA (US); Dennis Keith, Arlington, MA (US); John Finn, Stow, MA (US); Dale Christensen, Apex, NC (US); Tsvetelina Lazarova, Brookline, MA (US); Alan D. Watson, Lexington, MA (US); Yan Zhang, Sharon, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 39 days.

(21) Appl. No.: 09/738,742

(22) Filed: Dec. 15, 2000

(65) Prior Publication Data

US 2002/0025924 A1 Feb. 28, 2002

Related U.S. Application Data

(60) Provisional application No. 60/170,943, filed on Dec. 15, 1999.

(51) Int. Cl.$^7$ ................................................ C07K 7/50
(52) U.S. Cl. ........................ 530/317; 530/327; 514/11; 514/14
(58) Field of Search ................................ 530/317, 327; 514/11, 14

(56) References Cited

U.S. PATENT DOCUMENTS

| | | | |
|---|---|---|---|
| 4,396,543 A | 8/1983 | Debono | 260/112.5 R |
| 4,399,067 A | 8/1983 | Debono | 260/112.5 R |
| 4,482,487 A | 11/1984 | Abbott et al. | 260/112.5 R |
| 4,524,135 A | 6/1985 | Abbott et al. | 435/69 |
| 4,537,717 A | 8/1985 | Abbott et al. | 260/112.5 R |
| RE32,310 E | 12/1986 | Debono | 530/317 |
| RE32,311 E | 12/1986 | Debono | 530/317 |
| 5,573,936 A | 11/1996 | Kreuzman et al. | 435/196 |
| 5,629,288 A | 5/1997 | Lattrell et al. | 514/9 |
| 5,912,226 A | 6/1999 | Baker et al. | 514/9 |

FOREIGN PATENT DOCUMENTS

| | | |
|---|---|---|
| EP | 095 295 A | 11/1983 |
| EP | 178 152 A | 4/1986 |
| EP | 0 885 957 A1 | 12/1998 |
| WO | WO 99/43700 | 9/1999 |

OTHER PUBLICATIONS

Tally, F.P. et al., "Daptomycin: a Novel Agent for Gram–positive Infections," *Exp. Opin. Invest. Drugs* 8: 1223–1238 (1999).

Alborn, W. E. Jr. et al., "Daptomycin Disrupts Membrane Potential in Growing *Staphylococcus aureus*," *Antimicrobial Agents and Chemotherapy* 35: 2282–2287 (1991).
Allen, N. E. et al. "Inhibition of Peptidoglycan Biosynthesis in Gram–Positive Bacteria by LY146032," *Antimicrobial Agents and Chemotherapy* 31: 1093–1099 (1987).
Allen, N. E. et al. "Inhibition of Membrane Potential–Dependent Amino Acid Transport by Daptomycin," *Antimicrobial Agents and Chemotherapy* 35: 2639–2642 (1991).
Baltz, R. H., "Lipopeptide Antibiotics Produced by *Streptomyces roseosporus* and *Streptomyces fradiae*," in *Biotechnology of Antibiotics*, 2d Ed., 415–435 (1997).
Bingen, E. et al. "Bactericidal Activity of Daptomycin Against Vancomycin–Resistant *Enterococcus faecium* in an in Vitro Pharmacokinetic Model," *Eur. J. Clin. Microbiol. Infect. Dis.* 10: 1062–1065 (1991).
Boeck, LaVerne D. et al. "Deacylation of A21978C, An Acidic Lipopeptide Antibiotic Complex, by *Actinoplanes utahensis*," *Journal of Antibiotics* XLI: 1085–1092 (1988).
Boeck, L. D. et al. "A54145, A New Lipopeptide Antibiotic Complex: Discovery, Taxonomy, Fermentation and HPLC," *Journal of Antibiotics* XLIII: 587–593 (1990).
Champlin, Franklin R. et al. "Cell Envelope Impermeability to Daptomycin in *Pseudomonas aeruginosa* and *Pasteurella multocida*," *Current Microbiology* 21: 367–372 (1990).
Chong, Pei Pei et al. "Physical Identification of a Chromosomal Locus Encoding Biosynthetic Genes for the Lipopeptide Calcium–Dependent Antibiotic (CDA) of *Streptomyces coelicolor* A3(2)," *Microbiology* 144: 193–199 (1998).
Debono, M. et al. "A21978C, A Complex of New Acidic Peptide Antibiotics: Isolation, Chemistry, and Mass Spectral Structure Elucidation," *Journal of Antibiotics* XL: 761–777 (1987).
Debono, M. et al. "Enzymatic and Chemical Modifications of Lipopeptide Antibiotic A21978C: The Synthesis and Evaluation of Daptomycin (LY146032)," *Journal of Antibiotics* XLI: 1093–1105 (1988).
Debono, M. et al. "Synthesis of New Analogs of Echinocandin B by Enzymatic Deacylation and Chemical Reacylation of the Echinocandin B Peptide: Synthesis of the Antifungal Agent Cilofungin (LY121019)," *Journal of Antibiotics* XLII: 389–397 (1989).
Dong, Mei–Yan et al. "Treatment of *Clostridium difficile* Colitis in Hamsters with a Lipopeptide Antibiotic, LY146032," *Antimicrobial Agents and Chemotherapy* 31: 1135–1136 (1987).

(Continued)

*Primary Examiner*—Jon Weber
*Assistant Examiner*—David Lukton
(74) *Attorney, Agent, or Firm*—Timothy J. Douros; Jill M.N. Mandelblatt

(57) ABSTRACT

The present invention relates to novel lipopeptide compounds. The invention also relates to pharmaceutical compositions of these compounds and methods of using these compounds as antibacterial compounds. The invention also relates to methods of producing these novel lipopeptide compounds and intermediates used in producing these compounds.

31 Claims, No Drawings

OTHER PUBLICATIONS

Eid, Pascale et al. "Effect of Daptomycin on the Barotropic Behavior of Dioleoylphosphatidylglycerol: An Infrared Spectroscopic Investigation," *Chemistry and Physics of Lipids* 83: 131–140 (1996).

Eliopoulos, George M. et al. "In Vitro Activity and Mechanism of Action of A21978C$_1$, a Novel Cyclic Lipopeptide Antibiotic," *Antimicrobial Agents and Chemotherapy* 27: 357–362 (1985).

Huber, F. M. et al. "The Formation of Daptomycin by Supplying Decanoic Acid to *Streptomyces roseosporus* Cultures Producing the Antibiotic Complex A21978C," *Journal of Biotechnology* 7: 283–292 (1988).

Huber, F. M. et al. "The Synthesis of A21978C Analogs by *Streptomyces roseosporus* Cultivated Under Carbon Limitation and Fed Fatty Acids," *Biotechnology Letters* 12: 789–792 (1990).

Inokoshi, Junji et al. "Cloning and Sequencing of the Aculeacin A Acylase–Encoding Gene From *Actinoplanes utahensis* and Expression in *Streptomyces lividans*," *Gene* 119: 29–35 (1992).

Inokoshi, Junji et al. "Efficient Production of Aculeacin A Acylase in Recombinant *Streptomyces* strains," *Appl. Microbiol. Biotechnol.* 39: 532–536 (1993).

Kempter, Christoph et al. "CDA: Calcium–Dependent Peptide Antibiotics from *Streptomyces coelicolor* A3(2) Containing Unusual Residues," *Agnew. Chem. Int. Ed. Engl.* 36: 498–501 (1997).

Kirsch, Lee E. et al. "Kinetics of the Aspartyl Transpeptidation of Daptomycin, a Novel Lipopeptide Antibiotic," *Pharmaceutical Research* 6: 387–393 (1989).

Lakey, Jeremy H. et al. "The Role of Acyl Chain Character and Other Determinants on the Bilayer Activity of A21978C An Acidic Lipopeptide Antibiotic," *Biochimica et Biophysica Acta* 859: 219–226 (1986).

Lakey, Jeremy H. et al. "Fluorescence Indicates a Calcium–Dependent Interaction Between the Lipopeptide Antibiotic LY146032 and Phospholipid Membranes," *Biochemistry* 27: 4639–4645 (1988).

Lakey, Jeremy H. et al. "The Lipopeptide Antibiotic A21978C Has a Specific Interaction With DMPC Only in the Presence of Calcium Ions," *Biochimica et Biophysica Acta* 985: 60–66 (1989).

Lee, Belle L. et al. "Effect of Protein Binding of Daptomycin on MIC and Antibacterial Activity," *Antimicrobial Agents and Chemotherapy* 35: 2505–2508 (1991).

Liebowitz, Lynne D. et al. "In Vitro Selection of Bacteria Resistant to LY146032, a New Cyclic Lipopeptide," *Antimicrobial Agents and Chemotherapy* 32: 24–26 (1988).

Maget–Dana, Régine et al. "A Comparative Monomolecular Film Study of Antibiotic A21978C Homologues of Various Lipid Chain Length," *Biochimica et Biophysica Acta* 962: 201–207 (1988).

Zambias, Robert A. et al. "Preparation and Structure–Activity Relationships of Simplified Analogues of the Antifungal Agent Cilofungin: A Total Synthesis Approach," *Journal of Medicinal Chemistry* 35: 2843–2855 (1992).

Zmijewski, M.J. et al. "Role of Branched Chain Fatty Acid Precursors in Regulating Factor Profile in the Biosynthesis of A21978 C Complex," *Journal of Antibiotics* XXXIX: 1483–1485 (1986).

SEQUENCE LISTING

<160> NUMBER OF SEQ ID NOS: 1

<210> SEQ ID NO 1
<211> LENGTH: 38
<212> TYPE: PRT
<213> ORGANISM: Artificial
<220> FEATURE:
<223> OTHER INFORMATION: Synthetic

<400> SEQUENCE: 1

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Phe Pro Pro Arg
            20                  25                  30

Phe Pro Pro Arg Phe Pro
            35

LIPOPEPTIDES AS ANTIBACTERIAL AGENTS

FIELD OF THE INVENTION

The present invention relates to novel lipopeptide compounds. The invention also relates to pharmaceutical compositions of these compounds and methods of using these compounds as antibacterial compounds. The invention also relates to methods of producing these novel lipopeptide compounds and intermediates used in producing these compounds.

BACKGROUND OF THE INVENTION

The rapid increase in the incidence of gram-positive infections—including those caused by resistant bacteria—has sparked renewed interest in the development of novel classes of antibiotics. A class of compounds which have shown potential as useful antibiotics includes the A-21978C lipopeptides described in, for example, U.S. Pat. Nos. RE 32,333; RE 32,455; RE 32,311; RE 32,310; U.S. Pat. Nos. 4,482,487; 4,537,717; and 5,912,226. Daptomycin, a member of this class, has potent bactericidal activity in vitro and in vivo against clinically relevant gram-positive bacteria that cause serious and lifethreatening diseases. These bacteria include resistant pathogens, such as vancomycinresistant enterococci (VRE), methicillin resistant *Staphylococcus aureus* (MRSA), glycopeptide intermediate susceptible *Staphylococcus aureus* (GISA), coagulase-negative *staphylococci* (CNS), and penicillin-resistant *Streptococcus pneumoniae* (PRSP), for which there are few therapeutic alternatives. See, e.g., Tally et al., 1999, *Exp. Opin. Invest Drugs* 8:1223–1238.

Despite the promise that antibacterial agents such as daptomycin offer, the need for novel antibiotics continues. Many pathogens have been repeatedly exposed to commonly-used antibiotics. This exposure has led to the selection of variant antibacterial strains resistant to a broad spectrum of antibiotics The loss of potency and effectiveness of an antibiotic caused by resistant mechanisms renders the antibiotic ineffective and consequently can lead to life-threatening infections that are virtually untreatable. As new antibiotics come to market pathogens may develop resistance or intermediate resistance to these new drugs, effectively creating a need for a stream of new antibacterial agents to combat these emerging strains. In addition compounds that exhibit bacteriacidal activity would offer advantages over present bacteriastatic compounds. Thus, novel synthetic antibacterial agents would be expected to be useful to treat not only "natural" pathogens, but also intermediate drug resistant and drug resistant pathogens because the pathogen has never been exposed to the novel antibacterial agent. Additionally, new antibacterial agents may exhibit differential effectiveness against different types of pathogens.

SUMMARY OF THE INVENTION

The present invention addresses this problem by providing novel lipopeptide compounds which have antibacterial activity against a broad spectrum of bacteria, including drug-resistant bacteria. Further, the compounds of the present invention exhibit bacteriacidal activity.

The present invention comprises, in one aspect, antibacterial compounds of Formula I:

(I)

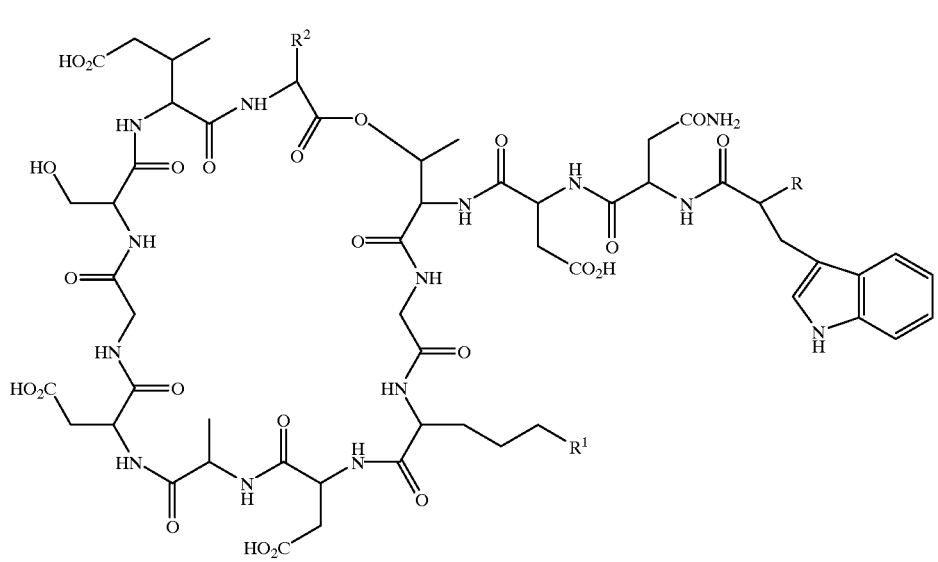

and salts thereof,
wherein R is:

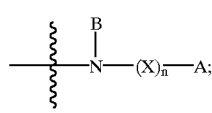

wherein X and X" are independently selected from C=O, C=S, C=NH, C=NR$^x$, S=O or SO$_2$;

wherein n is 0 or 1;

wherein $R^X$ is selected from alkyl, alkenyl, alkynyl, aryl, heteroaryl, cycloalkyl, heterocyclyl, hydroxyl, alkoxy, carboxy or carboalkoxy, wherein B is $X''R^Y$, H, alkyl, alkenyl, alkynyl, aryl, heteroaryl, cycloalkyl or heterocyclyl; and wherein $R^Y$ is selected from hydrido, alkyl, alkenyl, alkynyl, aryl, heteroaryl, cycloalkyl, heterocyclyl or hydroxyl.

In one aspect, A is H, $NH_2$, $NHR^A$, $NR^AR^B$, heteroaryl, cycloalkyl or heterocyclyl;

wherein $R^A$ and $R^B$ are independently selected from alkyl, alkenyl, alkynyl, aryl, heteroaryl, cycloalkyl, heterocyclyl or carboalkoxy;

wherein when n is 0, then A is additionally selected from

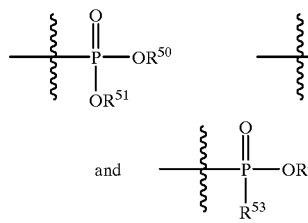

wherein each $R^{50}$–$R^{53}$ is independently selected from $(C_1$–$C_{15})$ alkyl, provided that when B is H and X is C=O, then A is other than (a) a pyridinyl ring substituted with a single $NHC(O)R^D$ substitutent or (b) a $(C_5$–$C_6)$ saturated cycloalkyl ring substituted with a single $NHC(O)R^D$ substitutent, wherein $R^D$ is $(C_1$–$C_{17})$ unsubstituted alkyl or $(C_2C_{17})$ unsubstituted alkenyl; and when B is H and n is 0, then A is not H.

In another aspect, A is aryl;

provided that when B is H and X is C=O, then A is other than a phenyl ring substituted with either:

(a) —O—(($C_8$–$C_{15}$) unsubstituted alkyl), wherein said phenyl ring may be further optionally substituted with one substituent selected from halo, nitro, $(C_1$–$C_3)$ alkyl, hydroxyl, $(C_1$–$C_3)$ alkoxy or $(C_1$–$C_3)$ alkylthio; or (b) —$NHC(O)R^D$, wherein the phenyl ring may be further optionally substituted with 1–2 substituents independently selected from amino, nitro, $(C_1$–$C_3)$ alkyl, hydroxyl, $(C_1$–$C_3)$ alkoxy, halo, mercapto, $(C_1$–$C_3)$ alkylthio, carbamyl or $(C_1$–$C_3)$ alkylcarbamyl; wherein $R^D$ is as defined previously.

In a third aspect of the invention, A is alkyl, alkenyl, alkynyl, alkoxy or aryloxy;

provided that when B is H and X is C=O, then A is other than (a) —($C_1$–$C_{16}$ unsubstituted alkyl)-$NH_2$;

(b) —($C_1$–$C_{10}$ unsubstituted alkyl)-$NHC(O)R^D$, wherein $R^D$ is as defined previously;

(c) —($C_1$–$C_{18}$)-alkyl, optionally substituted with up to one hydroxyl, carboxyl, or $C_1$–$C_3$ alkoxy, or one to three halo substituents;

(d) —($C_4$–$C_{18}$)-unsubstituted alkenyl;

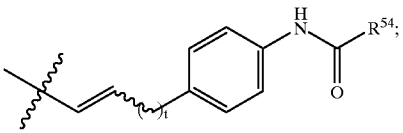

(e)

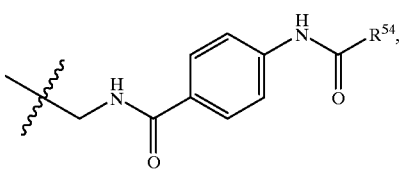

(f)

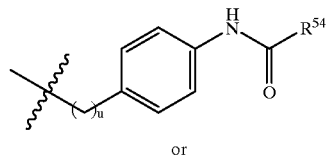

(g)

or

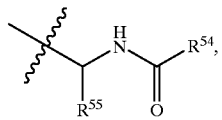

(h)

wherein $R^{54}$ is selected from $C_1$–$C_{17}$unsubstituted alkyl or $C_2$–$C_{17}$-unsubstituted alkenyl; wherein $R^{55}$ is selected from hydroxyethyl, hydroxymethyl, mercaptomethyl, mercaptoethyl, methylthioethyl, 2-thienyl, 3-indolemethyl, phenyl optionally substituted with a group selected from halo, nitro, $C_1$–$C_3$-unsubstituted alkyl, hydroxy, $C_1$–$C_3$-unsubstituted alkoxy, $C_1$–$C_3$-unsubsituted alkylthio, carbamyl or $C_1$–$C_3$ unsubstituted alkylcarbamyl; or benzyl optionally substituted with a group selected from halo, nitro, $C_1$–$C_3$-unsubstituted alkyl, hydroxy, $C_1$–$C_3$-unsubstituted alkoxy, $C_1$–$C_3$-unsubsituted alkylthio, carbamyl or $C_1$–$C_3$ unsubstituted alkylcarbamyl; wherein t is 0 or 1 and wherein u is an integer from 1–3; and when B is H and X is C=O, then X, together with A, does not form a carbamate amino protecting group; and when B is H and n is 0, then A is other than $C_4C_{14}$ unsubstituted alkyl.

In a fourth aspect, B and A together form a 5–7 membered heterocyclic or heteroaryl ring.

Wherein $R^1$ is

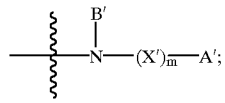

wherein X' and X''' are independently selected from C=O, C=S, C=NH, C=$NR^X$, S=O or $SO_2$;

wherein m is 0 or 1;

wherein $R^X$ is selected from alkyl, alkenyl, alkynyl, aryl, heteroaryl, cycloalkyl, heterocyclyl, hydroxyl, alkoxy, carboxy or carboalkoxy;

wherein B' is $X'''R^Y$, H, alkyl, alkenyl, alkynyl, aryl, heteroaryl, cycloalkyl or heterocyclyl;

wherein $R^Y$ is selected from hydrido, alkyl, alkenyl, alkynyl, aryl, heteroaryl, cycloalkyl, heterocyclyl or hydroxyl;

wherein A' is H, $NH_2$, $NHR^{A'}$, $NR^{A'}R^{B'}$, alkyl, alkenyl, alkynyl, alkoxy, aryloxy, aryl, heteroaryl, cycloalkyl or heterocyclyl;

wherein $R^{A'}$ and $R^{B'}$ are independently selected from alkyl, alkenyl, alkynyl, aryl, heteroaryl, cycloalkyl, heterocyclyl or carboalkoxy;

wherein when m is 0, then A' is additionally selected from:

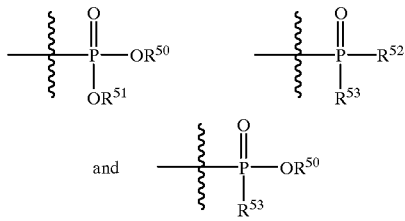

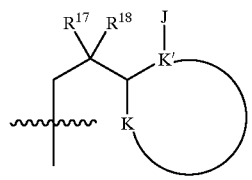

wherein each of $R^{50}$–$R^{53}$ is independently selected from $C_1$–$C_{15}$ alkyl, alternatively, wherein B' and A' together form a 5–7 membered heterocyclic or heteroaryl ring.

Wherein $R^2$ is

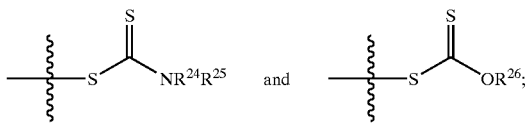

wherein K and K' together form a $C_3$–$C_7$ cycloalkyl or heterocyclyl ring or a $C_5$–$C_{10}$ aryl or heteroaryl ring;

wherein J is selected from the group consisting of hydrido, amino, $NHR^J$, $NR^JR^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo,

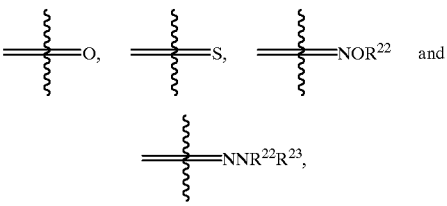

wherein each of $R^{24}$, $R^{25}$, and $R^{26}$ is independently selected from the group consisting of alkyl, cycloalkyl, heterocyclyl, aryl and heteroaryl; or $R^{24}$ and $R^{25}$ together form a 5–8 membered heterocyclyl ring;

wherein $R^J$ and $R^K$ are independently selected from alkyl, alkenyl, alkynyl, aryl, heteroaryl, cycloalkyl or heterocyclyl; or alternatively, wherein J, together with $R^{17}$, forms a 5–8 membered heterocyclyl or cycloalkyl ring; or alternatively, wherein J, together with both $R^{17}$ and $R^{18}$, forms a 5–8 membered aryl, cycloalkyl, heterocyclyl or heteroaryl ring; and wherein each of $R^{17}$ and $R^{18}$ is independently selected from the group consisting of hydrido, hydroxyl, halo, alkoxy, amino, thio, sulfinyl, sulfonyl and

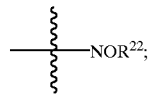

or wherein $R^{17}$ and $R^{18}$ taken together can form a group consisting of ketal, thioketal,

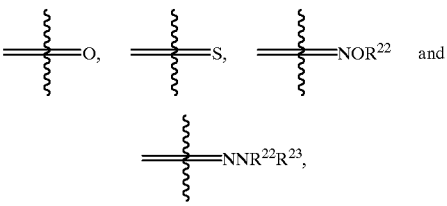

wherein each of $R^{22}$ and $R^{23}$ is independently selected from the group consisting of hydrido and alkyl.

In another embodiment, the invention also provides pharmaceutical compositions comprising compounds of Formula I and methods of use thereof.

In a further embodiment, the invention provides methods of making compounds of Formula I and pharmaceutical compositions thereof.

In an even further embodiment, the invention provides compounds useful as intermediates for the preparation of the compounds of Formula I In a still further embodiment, the invention provides methods of use of the compounds of Formula I to treat bacterial infections in humans

DETAILED DESCRIPTION OF THE INVENTION

Definitions

Molecular terms, when used in this application, have their common meaning unless otherwise specified.

The term "hydrido" denotes a single hydrogen atom (H)

The term "acyl" is defined as a carbonyl radical attached to an alkyl, alkenyl, alkynyl, cycloalkyl, heterocycyl, aryl or heteroaryl group, examples including, without limitation, such radicals as acetyl and benzoyl.

The term "amino" denotes a nitrogen radical containing two substituents independently selected from the group consisting of hydrido, alkyl, cycloalkyl, carboalkoxy, heterocyclyl, aryl, heteroaryl and sulfonyl. Subsets of the term amino are (1) the term "unsubstituted amino" which denotes an $NH_2$ radical, (2) the term "mono substituted amino" which is defined as a nitrogen radical containing a hydrido group and a substituent group selected from alkyl, cycloalkyl, heterocyclyl, aryl, or heteroaryl, and (3) the term "disubstituted amino" which is defined as a nitrogen radical containing two substituent groups independently selected from, alkyl, cycloalkyl, heterocyclyl, aryl, and heteroaryl. Preferred mono substituted amino radicals are "lower mono substituted amino" radicals, whereby the substituent group is a lower alkyl group. Preferred disubstituted amino radicals are "lower disubstituted amino" radicals, whereby the substituent groups are lower alkyl.

The term "acyloxy" denotes an oxygen radical adjacent to an acyl group.

The term "acylamino" denotes a nitrogen radical adjacent to an acyl group.

The term "carboalkoxy" is defined as a carbonyl radical adjacent to an alkoxy or aryloxy group.

The term "carboxyamido" denotes a carbonyl radical adjacent to an amino group.

The term "halo" is defined as a bromo, chloro, fluoro or iodo radical.

The term "thio" denotes a radical containing a substituent group independently selected from hydrido, alkyl, cycloalkyl, heterocyclyl, aryl and heteroaryl, attached to a divalent sulfur atom, such as, methylthio and phenylthio.

The term "alkyl" is defined as a linear or branched, saturated radical having one to about twenty carbon atoms unless otherwise specified. Preferred alkyl radicals are "lower alkyl" radicals having one to about five carbon atoms. One or more hydrogen atoms can also be replaced by a substitutent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, oxo, guanidino, formyl and an amino acid side chain. Examples of alkyl groups include, without limitation, methyl, tertbutyl, isopropyl, and methoxymethyl. Subsets of the term alkyl are (1) "unsubstituted alkyl" which is defined as an alkyl group that bears no substituent groups (2) "substituted alkyl" which denotes an alkyl radical in which (a) one or more hydrogen atoms is replaced by a substitutent group selected from acyl, acyloxy, carboalkoxy, carboxy, carboxyamido, cyano, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, N-acylaminosulfonyl or (b) two or more hydrogen atoms are each replaced by a substituent group independently selected from hydroxyl, carboxy, $C_1$–$C_3$ alkoxy, amino, acylamino, oxo or guanidino; and (3) the term "selected substituted alkyl" which denotes an alkyl radical in which (a) one proton is replaced by a group selected from hydroxyl, carboxy $C_1$–$C_3$ alkoxy, unsubstituted amino, acylamino, or acylamino phenyl or (b) one to three protons is replaced by a halo substituent.

The term "alkenyl" is defined as linear or branched radicals having two to about twenty carbon atoms, preferably three to about ten carbon atoms, and containing at least one carboncarbon double bond. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration. Examples of alkenyl groups include, without limitation, ethylenyl or phenyl ethylenyl.

The term "alkynyl" denotes linear or branched radicals having from two to about ten carbon atoms, and containing at least one carbon-carbon triple bond One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. An example of alkynyl group includes, without limitation, propynyl.

The term "aryl" or "aryl ring" denotes aromatic radicals in a single or fused carbocyclic ring system, having from five to fourteen ring members. In a preferred embodiment, the ring system has from six to ten ring members. One or more hydrogen atoms may also be replaced by a substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of aryl groups include, without limitation, phenyl, naphthyl, biphenyl, terphenyl. Subsets of the term aryl are (1) the term "phenyl" which denotes a compound of the formula.

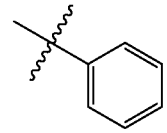

(2) the term "substituted phenyl" which is defined as a phenyl radical in which one or more protons are replaced by a substituent group selected from acyl, amino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino phenyl" denotes a phenyl radical in which one hydrogen atom is replaced by an acylamino group. One or more additional hydrogen atoms can also be replaced by a substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

"Heteroaryl" or "heteroaryl ring" denotes an aromatic radical which contain one to four hetero atoms or hetero groups selected from O, N, S,

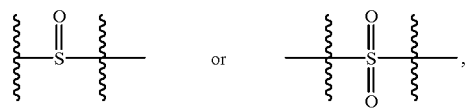

in a single or fused heterocyclic ring system, having from five to fifteen ring members. In a preferred embodiment, the heteroaryl ring system has from six to ten ring members, One or more hydrogen atoms may also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl. Examples of heteroaryl groups include, without limitation, pyridinyl, thiazolyl, thiadiazoyl, isoquinolinyl, pyrazolyl, oxazolyl, oxadiazoyl, triazolyl, and pyrrolyl groups. Subsets of the term heteroaryl are (1) the term "pyridinyl" which denotes compounds of the formula:

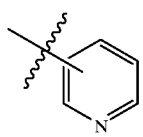

(2) the term "substituted pyridinyl" which is defined as a pyridinyl radical in which one or more protons is replaced by a substituent group selected from acyl, amino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino pyridinyl" which denotes a pyridinyl radical in which one hydrogen atom is replaced by an acylamino group, additionally, one or more additional hydrogen atoms can also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

The term "cycloalkyl" or "cycloalkyl ring" is defined as a saturated or partially unsaturated carbocyclic ring in a single or fused carbocyclic ring system having from three to twelve ring members. In a preferred embodiment, a cycloalkyl is a ring system having three to seven ring members. One or more hydrogen atoms may also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of a cycloalkyl group include, without limitation, cyclopropyl, cyclobutyl, cyclohexyl, and cycloheptyl.

The term "heterocyclyl," "heterocyclic" or "heterocyclyl ring" is defined as a saturated or partially unsaturated ring containing one to four hetero atoms or hetero groups selected from O, N, NH,

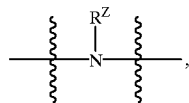

wherein $R^z$ is as defined for $R^x$,

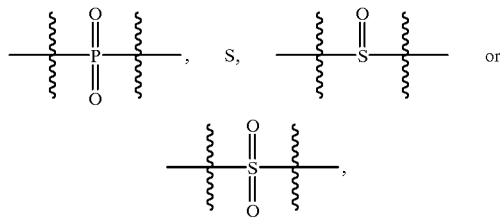

in a single or fused heterocyclic ring system having from three to twelve ring members. In a preferred embodiment, a heterocyclyl is a ring system having three to seven ring members One or more hydrogen atoms may also be replaced by a substituent group selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl Examples of a heterocyclyl group include, without limitation, morpholinyl, piperidinyl, and pyrrolidinyl.

The term "alkoxy" denotes oxy-containing radicals substituted with an alkyl, cycloalkyl or heterocyclyl group. Examples include, without limitation, methoxy, tert-butoxy, benzyloxy and cyclohexyloxy.

The term "aryloxy" denotes oxycontaining radicals substituted with an aryl or heteroaryl group. Examples include, without limitation, phenoxy.

The term "amino acid side chain" denotes any side chain (R group) from a naturally-occurring or a non-naturally occurring amino acid.

The term "sulfinyl" is defined as a tetravalent sulfur radical substituted with an oxo substituent and a second substituent selected from the group consisting of alkyl, cycloalkyl, heterocyclyl, aryl, or heteroaryl group.

The term "sulfonyl" is defined as a hexavalent sulfur radical substituted with two oxo substituents and a third substituent selected from alkyl, cycloalkyl, heterocyclyl aryl, or heteroaryl.

The term "carbamate amino protecting group" is defined as a recognized amino protecting group that when bound to an amino group forms a carbamate. Examples of carbamate amino protecting groups can be found in "Protective Groups in Organic Synthesis" by Theodora W. Greene, John Wiley and Sons, New York, 1981. Examples of carbamate amino protecting groups include benzyloxycarbonyl, t-butoxycarbonyl, t-amyloxycarbonyl, isobornyloxycarbonyl, adamantyloxycarbonyl, chlorobenzyloxycarbonyl, nitrobenzyloxycarbonyl or the like.

The salts of the compounds of the invention (preferably a compound of Formula I) include acid addition salts and base addition salts. In a preferred embodiment, the salt is a pharmaceutically acceptable salt of the compound of Formula I. The term "pharmaceutically-acceptable salts" embraces salts commonly used to form alkali metal salts and to form addition salts of free acids or free bases The nature of the salt is not critical, provided that it is pharmaceutically-acceptable. Suitable pharmaceutically-acceptable acid addition salts of the compounds of the invention (preferably a compound of Formula I) may be prepared from an inorganic acid or an organic acid. Examples of such inorganic acids include, without limitation, hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Suitable pharmaceutically-acceptable base addition salts of compounds of the invention (preferably a compound of Formula I) include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention (preferably a compound of Formula I) by treating, for example, the compound of the invention (preferably a compound of Formula I) with the appropriate acid or base.

The compounds of the invention (preferably compounds of Formula I) can possess one or more asymmetric carbon atoms and are thus capable of existing in the form of optical isomers as well as in the form of racemic or non-racemic mixtures thereof. The compounds of the invention (preferably compounds of Formula I) can be utilized in the present invention as a single isomer or as a mixture of stereochemical isomeric forms. Diastereoisomers, i.e., non-superimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention (preferably compounds of Formula I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention (preferably compounds of Formula I) can likewise be obtained by utilizing optically active starting materials. These isomers may be in the form of a free acid, a free base, an ester or a salt.

The invention also embraces isolated compounds. An isolated compound refers to a compound which represents at least 10%, preferably at least 20%, more preferably at least 50% and most preferably at least 80% of the compound present in the mixture. In a preferred embodiment, the compound, a pharmaceutically acceptable salt thereof, or a pharmaceutical composition comprising the compound exhibits a detectable (i.e. statistically significant) antimicrobial activity when tested in conventional biological assays such as those described herein.

Lipopeptide Compounds

The invention provides a compound of formula (I).

wherein X and X" are independently selected from C=O, C=S, C=NH, C=$NR^X$, S=O or $SO_2$;

wherein n is 0 or 1;

wherein $R^X$ is selected from alkyl, alkenyl, alkynyl, aryl, heteroaryl, cycloalkyl, heterocyclyl, hydroxyl, alkoxy, carboxy or carboalkoxy;

wherein B is X"$R^Y$, H, alkyl, alkenyl, alkynyl, aryl, heteroaryl, cycloalkyl or heterocyclyl; and wherein $R^Y$ is selected from hydrido, alkyl, alkenyl, alkynyl, aryl, heteroaryl, cycloalkyl, heterocyclyl or hydroxyl.

In one aspect, A is H, $NH_2$, $NHR^A$, $NR^A R^B$, heteroaryl, cycloalkyl or heterocyclyl;

wherein $R^A$ and $R^B$ are independently selected from alkyl, alkenyl, alkynyl, aryl, heteroaryl, cycloalkyl, heterocyclyl or carboalkoxy;

wherein when n is 0, then A is additionally selected from:

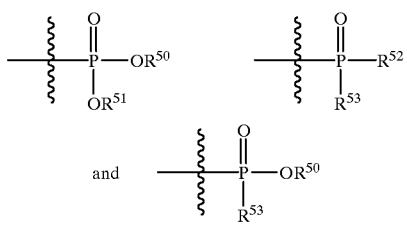

wherein each $R^{50}$–$R^{53}$ is independently selected from ($C_1$–$C_{15}$) alkyl, provided that when B is H and X is C=O, then A is other than (a) a pyridinyl ring substituted with a single NHC(O)$R^D$ substitutent or (I)

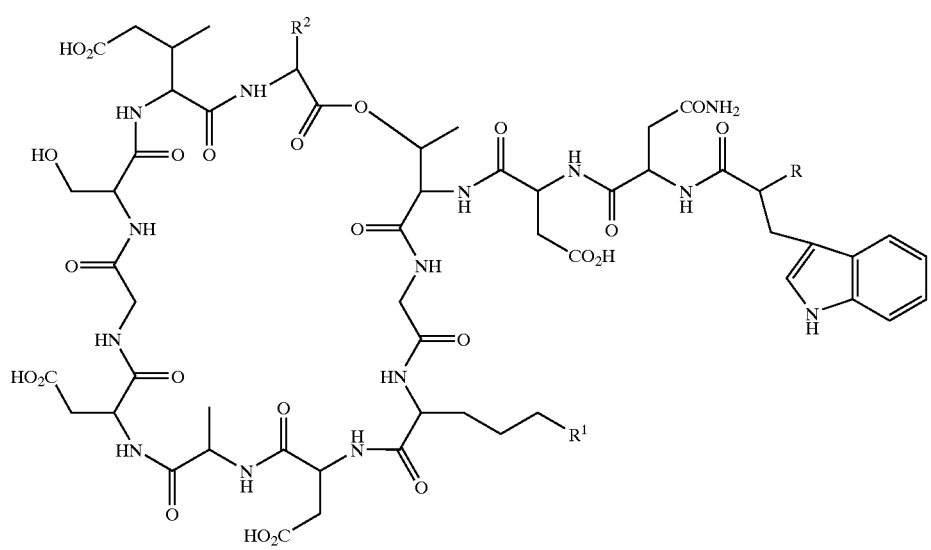

and salts thereof, wherein R is:

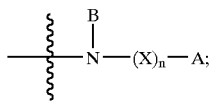

(b) a ($C_5$–$C_6$) saturated cycloalkyl ring substituted with a single NHC(O)$R^D$ substitutent, wherein $R^D$ is ($C_1$–$C_{17}$) unsubstituted alkyl or ($C_2$–$C_{17}$) unsubstituted alkenyl; and
when B is H and n is 0, then A is not H.

In another aspect, A is aryl;
provided that when B is H and X is C=O, then A is other than a phenyl ring substituted with either:

(a) —O—(($C_8$–$C_{15}$) unsubstituted alkyl), wherein said phenyl ring may be further optionally substituted with one substituent selected from halo, nitro, ($C_1$–$C_3$) alkyl, hydroxyl, ($C_1$–$C_3$) alkoxy or ($C_1$–$C_3$) alkylthio; or (b) —NHC(O)$R^D$, wherein the phenyl ring may be further optionally substituted with 1–2 substituents independently selected from amino, nitro, ($C_1$–$C_3$) alkyl, hydroxyl, ($C_1$–$C_3$) alkoxy, halo, mercapto, ($C_1$–$C_3$) alkylthio, carbamyl or ($C_1$–$C_3$) alkylcarbamyl; wherein $R^D$ is as defined previously.

In a third aspect of the invention, A is alkyl, alkenyl, alkynyl, alkoxy or aryloxy;
provided that when B is H and X is C=O, then A is other than (a) —($C_1$–$C_{16}$ unsubstituted alkyl)-$NH_2$;

(b) —($C_1$–$C_{10}$ unsubstituted alkyl)-NHC(O)$R^D$, wherein $R^D$ is as defined previously;

(c) —($C_1$–$C_{18}$)-alkyl, optionally substituted with up to one hydroxyl, carboxyl or $C_1$–$C_3$ alkoxy, or one to three halo substituents;

(d) —($C_4$–$C_{18}$)-unsubstituted alkenyl;

(e)

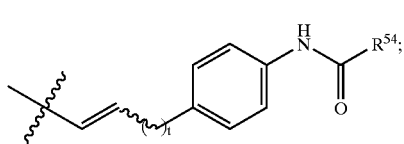

(f)

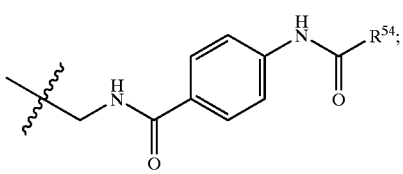

(g)

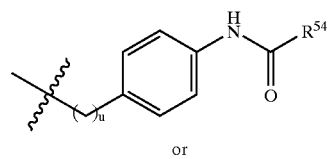

or (h)

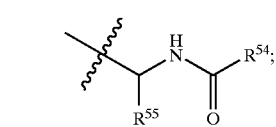

wherein $R^{54}$ is selected from $C_1$–$C_{17}$-unsubstituted alkyl or $C_2$–$C_{17}$-unsubstituted alkenyl; wherein $R^{55}$ is selected from hydroxyethyl, hydroxymethyl, mercaptomethyl, mercaptoethyl, methylthioethyl, 2-thienyl, 3-indolemethyl, phenyl optionally substituted with a group selected from halo, nitro, $C_1$–$C_3$-unsubstituted alkyl, hydroxy, $C_1$–$C_3$-unsubstituted alkoxy, $C_1$–$C_3$-unsubsituted alkylthio, carbamyl or $C_1$–$C_3$-unsubstituted alkylcarbamyl; or benzyl optionally substituted with a group selected from halo, nitro, $C_1$–$C_3$-unsubstituted alkyl, hydroxy, $C_1$–$C_3$-unsubstituted alkoxy, $C_1$–$C_3$-unsubsituted alkylthio, carbamyl or $C_1$–$C_3$ unsubstituted alkylcarbamyl; wherein t is 0 or 1 and wherein u is an integer from 1–3; and when B is H and X is C=O, then X, together with A, does not form a carbamate amino protecting group; and when B is H and n is 0, then A is other than $C_4$–$C_{14}$ unsubstituted alkyl.

In a fourth aspect, B and A together form a 5–7 membered heterocyclic or heteroaryl ring.

Wherein $R^1$ is

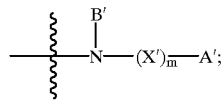

wherein X' and X'" are independently selected from C=O, C=S, C=NH, C=$NR^X$, S=O or $SO_2$;
wherein m is 0 or 1;
wherein $R^X$ is selected from alkyl, alkenyl, alkynyl, aryl, heteroaryl, cycloalkyl, heterocyclyl, hydroxyl, alkoxy, carboxy or carboalkoxy;
wherein B' is X'" $R^Y$, H, alkyl, alkenyl, alkynyl, aryl, heteroaryl, cycloalkyl or heterocyclyl;
wherein $R^Y$ is selected from hydrido, alkyl, alkenyl, alkynyl, aryl, heteroaryl, cycloalkyl, heterocyclyl or hydroxyl;
wherein A' is H, $NH_2$, $NHR^{A'}$, $NR^{A'}R^{B'}$, alkyl, alkenyl, alkynyl, alkoxy, aryloxy, aryl, heteroaryl, cycloalkyl or heterocyclyl;
wherein $R^{A'}$ and $R^{B'}$ are independently selected from alkyl, alkenyl, alkynyl, aryl, heteroaryl, cycloalkyl, heterocyclyl or carboalkoxy;
wherein when m is 0, then A' is additionally selected from

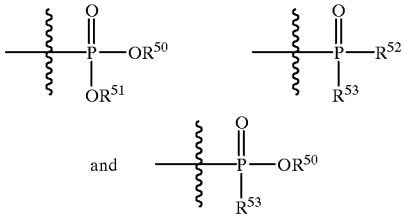

and wherein each of $R^{50}$–$R^{53}$ is independently selected from $C_1$–$C_{15}$ alkyl;
alternatively, wherein B' and A' together form a 5–7 membered heterocyclic or heteroaryl ring.

Wherein $R^2$ is

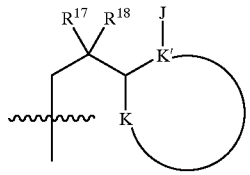

wherein K and K' together form a $C_3$–$C_7$ cycloalkyl or heterocyclyl ring or a $C_5$–$C_{10}$ aryl or heteroaryl ring;
wherein J is selected from the group consisting of hydrido, amino, $NHR^J$, $NR^JR^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo,

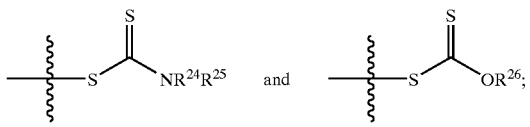

wherein each of $R^{24}$, $R^{25}$, and $R^{26}$ is independently selected from the group consisting of alkyl, cycloalkyl, heterocyclyl, aryl and heteroaryl; or $R^{24}$ and $R^{25}$ together form a 5–8 membered heterocyclyl ring;

wherein $R^J$ and $R^K$ are independently selected from alkyl, alkenyl, alkynyl, aryl, heteroaryl, cycloalkyl or heterocyclyl; or alternatively, wherein J, together with $R^{17}$, forms a 5–8 membered heterocyclyl or cycloalkyl ring; or alternatively, wherein J, together with both $R^{17}$ and $R^{18}$, forms a 5–8 membered aryl, cycloalkyl, heterocyclyl or heteroaryl ring; and wherein each of $R^{17}$ and $R^{18}$ is independently selected from the group consisting of hydrido, halo, hydroxyl, alkoxy, amino, thio, sulfinyl, sulfonyl and

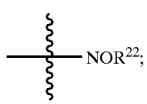

or wherein $R^{17}$ and $R^{18}$ taken together can form a group consisting of ketal, thioketal,

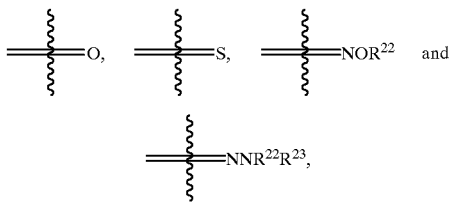

wherein each of $R^{22}$ and $R^{23}$ is independently selected from the group consisting of hydrido and alkyl In a preferred embodiment of the invention, R is selected from

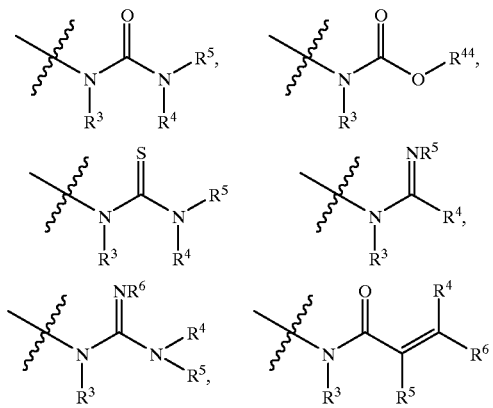

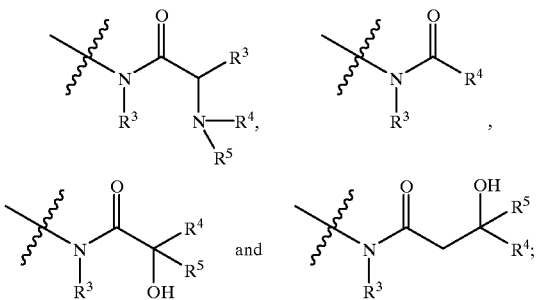

wherein each of $R^3$, $R^4$ $R^5$, and $R^6$ is independently selected from the group consisting of hydrido, alkyl, aryl, heterocyclyl and heteroaryl, and wherein $R^{44}$ is selected from the group consisting of alkyl, aryl, heterocyclyl and heteroaryl.

In a more preferred embodiment of the invention R is selected from

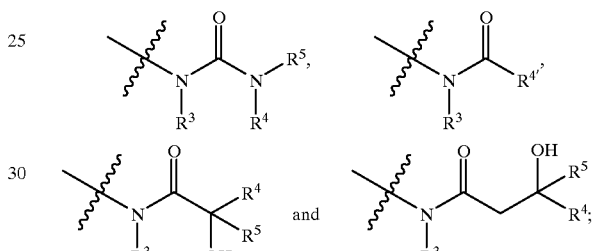

wherein $R^{4'}$ is selected from the group consisting of alkyl, substituted alkyl, substituted phenyl, heteroaryl, heterocyclyl, optionally substituted ($C_8$–$C_{14}$)straight chain alkyl and

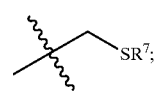

wherein $R^7$ is an alkyl group.

In an even more preferred embodiment of the invention, R is

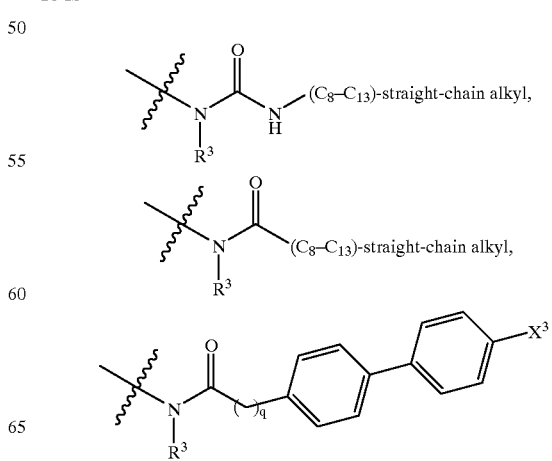

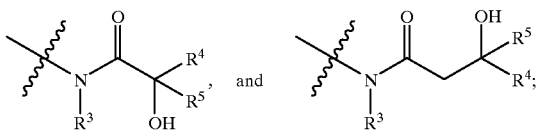

wherein $X^3$ is chloro or trifluoromethyl and wherein q is 0 or 1.

In a preferred embodiment of the invention, $R^1$ is selected from the group consisting of:

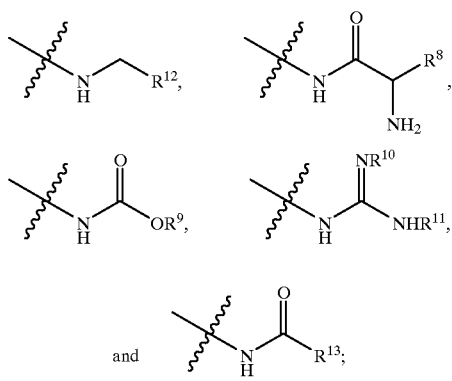

wherein $R^8$ is selected from an amino acid side chain, wherein said amino acid side chain may be one that is naturally occurring or one that is not naturally occurring, wherein each of $R^9$, $R^{10}$ and $R^{11}$ is selected from hydrido, alkyl, aryl, heterocyclyl and heteroaryl; wherein $R^{12}$ is selected from the group consisiting of heterocyclyl, heteroaryl, aryl, and alkyl and wherein $R^{13}$ is selected from $(C_1-C_3)$alkyl and aryl.

In a more preferred embodiment of the invention, $R^1$ is selected from the group consisting of

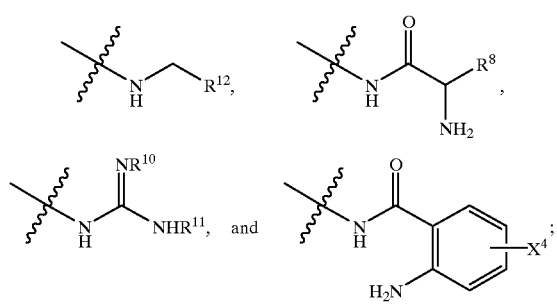

wherein $R^8$ is selected from tryptophan side chain and lysine side chain; wherein each of $R^{10}$ and $R^{11}$ is independently selected from hydrido and alkyl; wherein $R^{12}$ is selected from imidazolyl, N-methylimidazolyl, indolyl, quinolinyl, benzyloxybenzyl, and benzylpiperidenylbenzyl; and wherein $X^4$ is selected from fluoro and trifluoromethyl.

In a preferred embodiment of $R^2$, J is selected from the group consisting of hydrido, amino, azido and

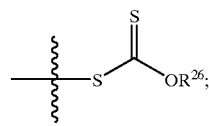

wherein $R^{17}$ and $R^{18}$ taken together form a group selected from the group consisting of ketal,

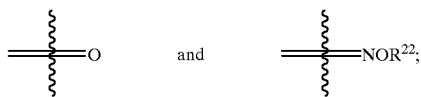

alternatively, $R^{17}$ is hydroxyl when $R^{18}$ is hydrido. Alternatively, wherein J, together with $R^{17}$, forms a heterocyclyl ring.

In a more preferred embodiment of the invention, $R^2$ is selected from

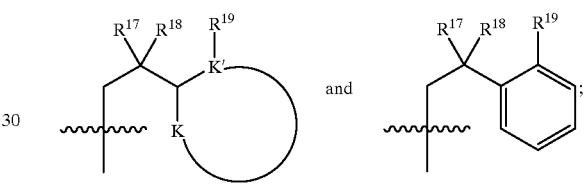

wherein $R^{17}$ and $R^{18}$ taken together form a group selected from

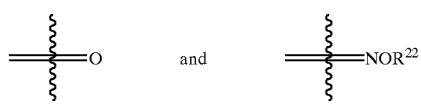

wherein $R^{22}$ is selected from the group consisting of H and alkyl; wherein $R^{19}$ is selected from the group consisting of hydrido, amino, azido and

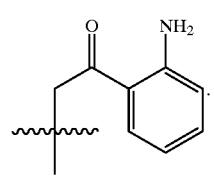

In an even more preferred embodiment of the invention $R^2$ is

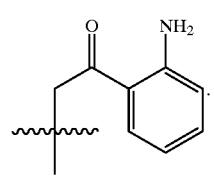

Table I provides exemplary compounds of Formula I:

TABLE I

| Cpd # | R | R¹ | R² | Mass Spec | Synth Ex # |
|---|---|---|---|---|---|
| 1 | NHCONH(CH$_2$)$_7$CH$_3$ | NH$_2$ | 2-aminophenyl ketone | 1622.8 | 1 |
| 2 | NHCONH(CH$_2$)$_{11}$CH$_3$ | NH$_2$ | 2-aminophenyl ketone | 1665 | 2 |
| 3 | NHCONH(CH$_2$)$_{10}$CH$_3$ | methyl-tryptophan amide | 2-aminophenyl ketone | 1951 | 3 |
| 5 | 4'-chlorobiphenyl-4-carboxamide | methyl-tryptophan amide | 2-aminophenyl ketone | 1867 | 3 |
| 6 | ornithine-NHTs | methyl-tryptophan amide | 2-aminophenyl ketone | 1935 | 3 |
| 7 | NH(CH$_2$)$_8$CH$_3$ | methyl-tryptophan amide | 2-aminophenyl ketone | 1779 | 3a |
| 8 | NHCO(CH$_2$)$_8$CO$_2$CH$_3$ | methyl-tryptophan amide | 2-aminophenyl ketone | 1851 | 3 |
| 9 | NHCO(CH$_2$)$_6$CO$_2$CH$_3$ | methyl-tryptophan amide | 2-aminophenyl ketone | 1823 | 3 |
| 10 | NHCO(CH$_2$)$_6$NHBoc | NHBoc-tryptophan amide | 2-aminophenyl ketone | 1980 | 3 |

TABLE I-continued

| Cpd # | R | R¹ | R² | Mass Spec | Synth Ex # |
|---|---|---|---|---|---|
| 11 | NHCO(CH₂)₇NHBoc | tryptophan-NHBoc amide | 2-aminophenyl ketone | 1894 | 3 |
| 12 | NHCO(CH₂)₁₀NHBoc | tryptophan-NHBoc amide | 2-aminophenyl ketone | 1936 | 3 |
| 13 | NHCO(CH₂)₁₁NHBoc | tryptophan-NHBoc amide | 2-aminophenyl ketone | 1950 | 3 |
| 17 | NHCONH(CH₂)₁₁CH₃ | α-methyl-tryptophan amide | 2-aminophenyl ketone | 1865 | 3b |
| 18 | 4'-chlorobiphenyl-4-carboxamide | NH₂ | 2-aminophenyl ketone | 1696 | 1a |
| 19 | 2-phenylthiazol-4-yl-acetamide | NH₂ | 2-aminophenyl ketone | 1668 | 1 |
| 20 | 4-chlorophenylacetamide | α-methyl-tryptophan amide | 2-aminophenyl ketone | 1807 | 3 |
| 21 | 2,4-dichlorophenylacetamide | α-methyl-tryptophan amide | 2-aminophenyl ketone | 1841 | 3 |
| 22 | 4-phenoxyphenylacetamide | α-methyl-tryptophan amide | 2-aminophenyl ketone | 1864 | 3 |

TABLE I-continued
| Cpd # | R | R¹ | R² | Mass Spec | Synth Ex # |
|---|---|---|---|---|---|
| 23 |  |  |  | 1843 | 3 |
| 24 |  | 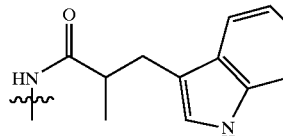 | 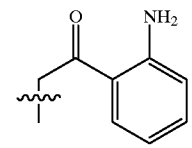 | 1882 | 3 |
| 25 | 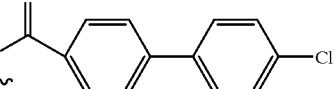 | 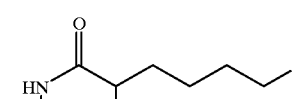 | 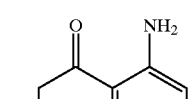 | 1823.3 | 4 |
| 34 | 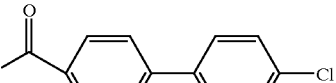 | 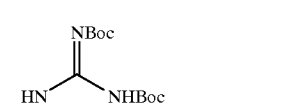 | 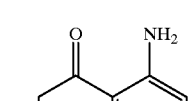 | 1738 | 3 |
| 35 | 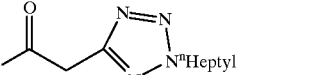 | 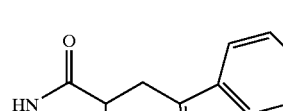 | 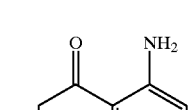 | 1862 | 3 |
| 36 | 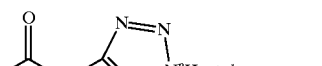 | 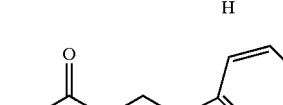 | 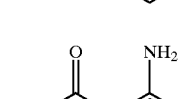 | 1962 | 3 |
| 40 |  | NH₂ | 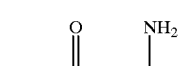 | 1736 | 1 |
| 41 |  | NHBoc | 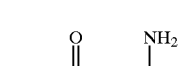 | 1836 | 1 |
| 43 |  | NHBoc | 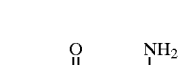 | 1624 | 1 |

TABLE I-continued

| Cpd # | R | R¹ | R² | Mass Spec | Synth Ex # |
|---|---|---|---|---|---|
| 44 | (5-chlorobenzothiophen-3-yl)acetamide group | NHBoc | 2-aminobenzoyl group | 1675 | 1 |
| 48 | NHCONH(CH$_2$)$_{10}$CH$_3$ | NH$_2$ | 2-aminobenzoyl group | 1665 | 2a |
| 49 | [2-(4-chlorophenyl)thiazol-4-yl]acetamide group | NH$_2$ | 2-aminobenzoyl group | 1703 | 1 |
| 50 | 4'-chlorobiphenyl-4-carboxamide group | guanidino group | 2-aminobenzoyl group | 1738.8 | 3 |
| 56 | NHCONH(CH$_2$)$_7$CH$_3$ | N,N'-di-Boc-lysinamide group | 2-aminobenzoyl group | 1950 | 4 |
| 57 | NHCONH(CH$_2$)$_{10}$CH$_3$ | N,N'-di-Boc-lysinamide group | 2-aminobenzoyl group | 1992 | 4 |
| 58 | NHCONH(CH$_2$)$_{11}$CH$_3$ | N,N'-di-Boc-lysinamide group | 2-aminobenzoyl group | 2006 | 4 |
| 62 | NHCONH(CH$_2$)$_7$CH$_3$ | lysinamide group | 2-aminobenzoyl group | 1750 | 4 |
| 63 | NHCONH(CH$_2$)$_{10}$CH$_3$ | lysinamide group | 2-aminobenzoyl group | 1792 | 4 |

TABLE I-continued

| Cpd # | R | R¹ | R² | Mass Spec | Synth Ex # |
|---|---|---|---|---|---|
| 64 | NHCONH(CH$_2$)$_{11}$CH$_3$ | lysine-derived acyl group | 2-aminobenzoyl | 1806 | 4 |
| 69 | NHCONH(CH$_2$)$_7$CH$_3$ | α-methyl-tryptophan-derived acyl group | 2-aminobenzoyl | 1808 | 4 |
| 70 | NHCONH(CH$_2$)$_7$CH$_3$ | 2-amino-6-fluorobenzamide | 2-aminobenzoyl | 1759 | 4 |
| 71 | NHCONH(CH$_2$)$_7$CH$_3$ | guanidine | 2-aminobenzoyl | 1650 | 3 |
| 75 | NHCONH(CH$_2$)$_{10}$CH$_3$ | N,N'-di-Boc-guanidine | 2-aminobenzoyl | 1706.9 | 3 |
| 76 | NHCONH(CH$_2$)$_7$CH$_3$ | (5-methoxy-1H-indol-3-yl)methylamino | 2-aminobenzoyl | 1780.9 | 4a |
| 77 | NHCONH(CH$_2$)$_7$CH$_3$ | (1H-imidazol-2-yl)methylamino | 2-aminobenzoyl | 1701.8 | 4a |
| 78 | NHCONH(CH$_2$)$_7$CH$_3$ | (6-nitroquinolin-2-yl)methylamino | 2-aminobenzoyl | 1807.9 | 4a |
| 87 | NHCONH(CH$_2$)$_{11}$CH$_3$ | (5-methoxy-1H-indol-3-yl)methylamino | 2-aminobenzoyl | 1757.9 | 4a |

TABLE I-continued

| Cpd # | R | R¹ | R² | Mass Spec | Synth Ex # |
|---|---|---|---|---|---|
| 88 | NHCONH(CH$_2$)$_{11}$CH$_3$ | HN-CH$_2$-(6-nitroquinolin-2-yl) | 2-aminobenzoyl | 1864 | 4a |
| 89 | NHCONH(CH$_2$)$_{11}$CH$_3$ | HN-CH$_2$-(1H-imidazol-2-yl) | 2-aminobenzoyl | 1837 | 4a |
| 100 | HN-C(O)-CH(NH$_2$)-(CH$_2$)$_6$CH$_3$ | NH$_2$ | 2-aminobenzoyl | 1635.7 | 1 |
| 106 | HN-C(O)-(4'-chloro-biphenyl-4-yl) | 2-amino-6-fluorobenzamido | 2-aminobenzoyl | 1832 | 4 |
| 108 | NHCONH(CH$_2$)$_{10}$CH$_3$ | 2-amino-6-fluorobenzamido | 2-aminobenzoyl | 1801 | 4 |
| 113 | NHCONH(CH$_2$)$_{10}$CH$_3$ | HN-CH$_2$-(1H-imidazol-2-yl) | 2-aminobenzoyl | 1743 | 4a |
| 114 | NHCONH(CH$_2$)$_{10}$CH$_3$ | HN-CH$_2$-(5-methoxy-1H-indol-3-yl) | 2-aminobenzoyl | 1822 | 4b |
| 115 | HN-C(O)-(4'-trifluoromethyl-biphenyl-4-yl) | NHBoc | 2-aminobenzoyl | 1828.8 | 1 |
| 116 | HN-C(O)-(4'-trifluoromethyl-biphenyl-4-yl) | NH$_2$ | 2-aminobenzoyl | 1729 | 1 |

TABLE I-continued

| Cpd # | R | R¹ | R² | Mass Spec | Synth Ex # |
|---|---|---|---|---|---|
| 117 | NHCONH(CH$_2$)$_8$CH$_3$ | NHBoc | 2-aminophenyl-C(O)CH< | 1636.6 | 2b |
| 118 | NHCONH(CH$_2$)$_8$CH$_3$ | NH$_2$ | 2-aminophenyl-C(O)CH< | 1636.6 | 2b |
| 119 | NHCONH(CH$_2$)$_9$CH$_3$ | NHBoc | 2-aminophenyl-C(O)CH< | 1650.1 | 2c |
| 120 | NHCONH(CH$_2$)$_9$CH$_3$ | NH$_2$ | 2-aminophenyl-C(O)CH< | 1650.2 | 2c |
| 123 | NHCOCH$_2$S(CH$_2$)$_{11}$CH$_3$ | NH$_2$ | 2-aminophenyl-C(O)CH< | 1709 | 1 |
| 124 | NHCOCH$_2$S(CH$_2$)$_{10}$CH$_3$ | NH$_2$ | 2-aminophenyl-C(O)CH< | 1695 | 1 |
| 125 | NHCOCH$_2$S(CH$_2$)$_9$CH$_3$ | NH$_2$ | 2-aminophenyl-C(O)CH< | 1681 | 1 |

Preferred compounds of Formula I are composed 2, compound 3, compound 18, compound 48, compound 89, compound 116, compund 118, and compound 120.

Other preferred compounds include a compound of Formula (I').

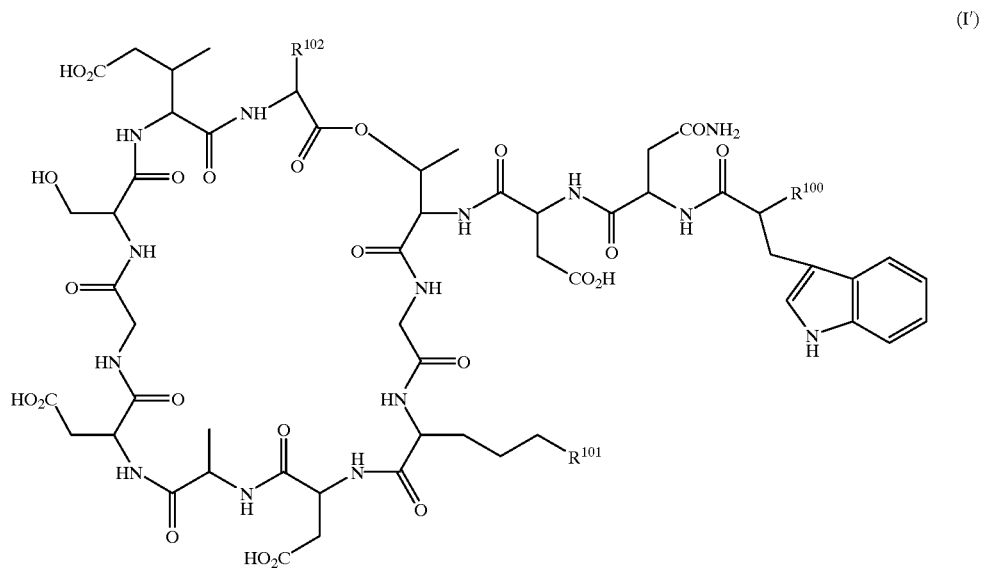

(I')

wherein $R^{100}$, $R^{101}$ and $R^{102}$ are as defined in Table II.

TABLE II

| Cpd # | $R^{100}$ | $R^{101}$ | $R^{102}$ | Mass Spec | Synth Ex # |
|---|---|---|---|---|---|
| 72 | HN–C(=O)–CH(OH)–(CH₂)₈CH₃ | NHBoc | –CH₂–C(=O)–(2-NH₂-C₆H₄) | 1764.5 | 1 |
| 73 | HN–C(=O)–CH(OH)–(CH₂)₁₁CH₃ | NHBoc | –CH₂–C(=O)–(2-NH₂-C₆H₄) | 1792.5 | 1 |
| 74 | HN–C(=O)–CH₂–CH(OH)–(CH₂)₁₂CH₃ | NHBoc | –CH₂–C(=O)–(2-NH₂-C₆H₄) | 1820.5 | 1 |
| 109 | NHCOCHCH(CH₂)₇CH₃ | NHBoc | –CH₂–C(=O)–(2-NH₂-C₆H₄) | 1651.8 | 1b |

TABLE II-continued

| Cpd # | R^100 | R^101 | R^102 | Mass Spec | Synth Ex # |
|---|---|---|---|---|---|
| 110 | NHCOCHCH(CH$_2$)$_9$CH$_3$ | NHBoc | 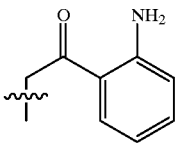 | 1679.9 | 1b |
| 111 | NHCOCHCH(CH$_2$)$_7$CH$_3$ | NH$_2$ | 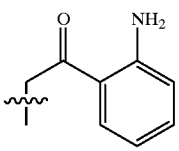 | 1680 | 1b |
| 112 | NHCOCHCH(CH$_2$)$_9$CH$_3$ | NH$_2$ | 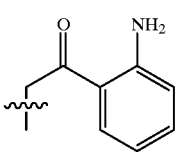 | 1680 | 1b |

According to a preferred embodiment, the present invention provides one or more crystalline forms of compound of formula (I), and salts thereof.

Lipopeptide Intermediates

The present invention also provides compounds that are particularly useful as intermediates for the preparation of the compounds of Formula I. These compounds may also have antibacterial properties, as discussed above. In one aspect of the invention, compounds of Formula II are provided:

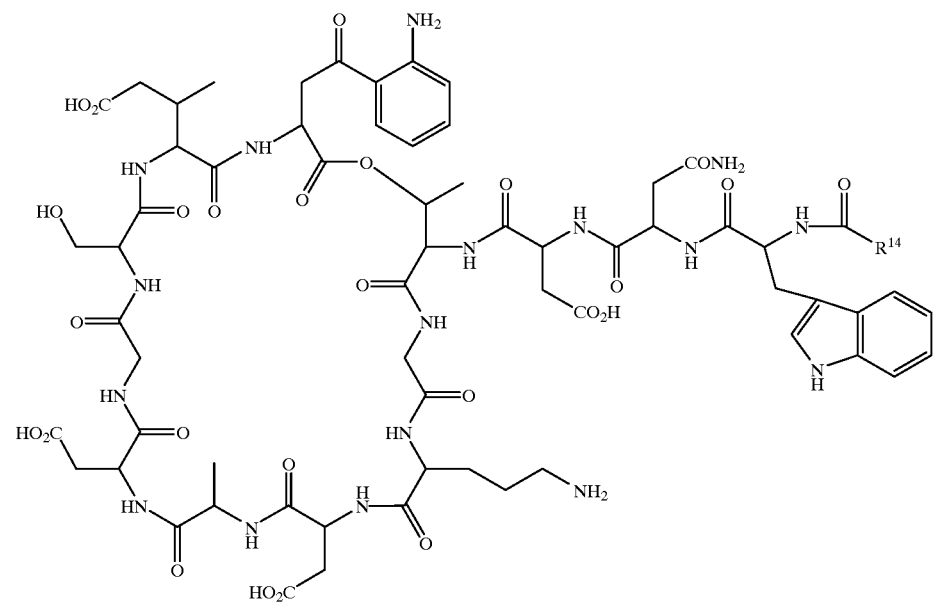

(II)

wherein $R^{14}$ is selected from the group consisting of

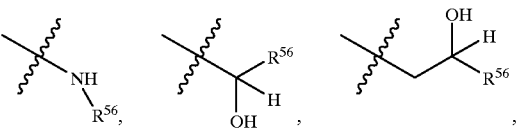

-continued and 

wherein $R^{56}$ is an optionally substituted straight-chain $C_8$–$C_{14}$ alkyl group and wherein q' is 0–3.

Compounds 1, 2, 18, 48, 116, 118 and 120 are useful both as antibacterial compounds and as intermediates in the synthesis of compounds of this invention.

Compounds 72, 73 and 74 as well as the formula (II) compounds in Table III are other preferred compounds that are useful as antibacterial compounds and as intermediates in the synthesis of compounds of this invention:

TABLE III

| Compound # | $R^{14}$ |
|---|---|
| 45 | —CH(OH)(CH$_2$)$_5$CH$_3$ |
| 37 | —CH(OH)(CH$_2$)$_6$CH$_3$ |
| 46 | —CH(OH)(CH$_2$)$_7$CH$_3$ |
| 38 | —CH(OH)(CH$_2$)$_8$CH$_3$ |

TABLE III-continued

| Compound # | $R^{14}$ |
|---|---|
| 47 | —CH(OH)(CH$_2$)$_9$CH$_3$ |
| 39 | —CH(OH)(CH$_2$)$_{10}$CH$_3$ |

Table IV provides another set of formula (II) compounds that are useful as intermediates in the synthesis of compounds of this invention:

TABLE IV

| Compound # | $R^{14}$ |
|---|---|
| 150 | (CH$_2$)$_7$CH$_3$ |
| 151 | (CH$_2$)$_8$CH$_3$ |
| 152 | (CH$_2$)$_9$CH$_3$ |
| 153 | (CH$_2$)$_{10}$CH$_3$ |
| 154 | (CH$_2$)$_{11}$CH$_3$ |
| 155 | (CH$_2$)$_{12}$CH$_3$ |

In another aspect of the invention, compounds of Formula III are provided as useful intermediates for the preparation of compounds of Formula I and/or antibacterial compounds:

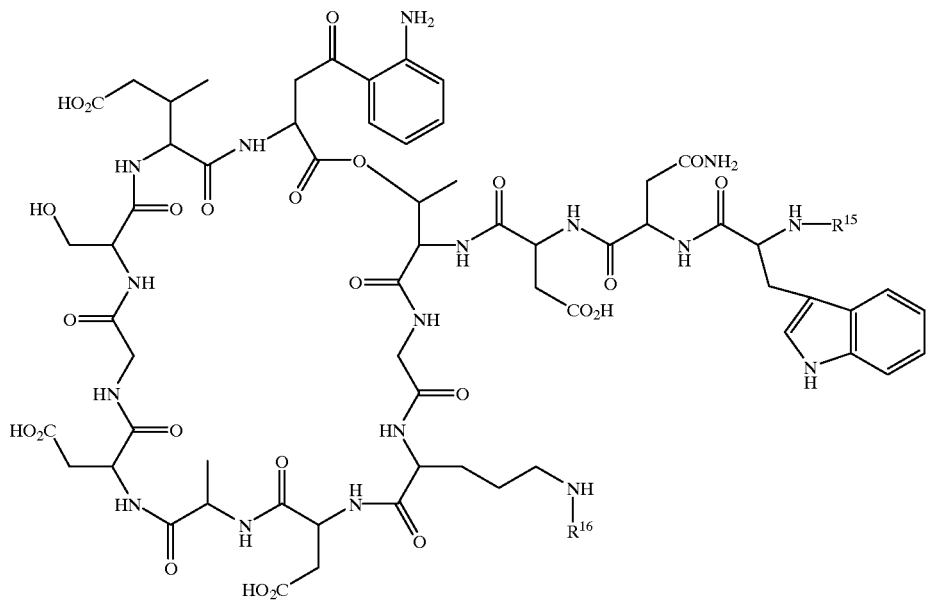

(III)

wherein $R^{15}$ is selected from hydrido and a carbamate amino protecting group, preferably a tert-butoxycarbonyl group; wherein $R^{16}$ is selected from the group consisting of

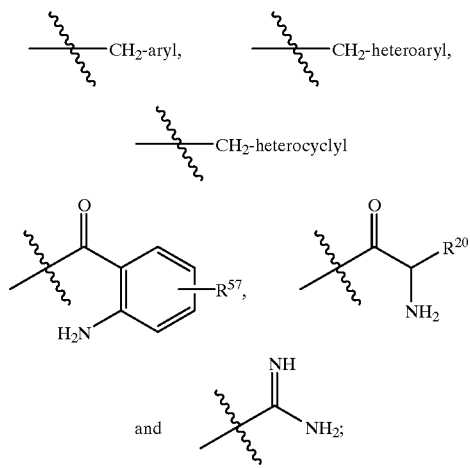

wherein $R^{57}$ is a halo or halo substituted alkyl group, preferably a fluoro or trifluoromethyl group; wherein, $R^{20}$ is an amino acid side chain, preferably a lysine or tryptophan side chain.

Lipopeptide Compound Pharmaceutical Compositions and Methods of Use thereof

Another object of the instant invention is to provide lipopeptide compounds or salts thereof, as well as pharmaceutical compositions or formulations comprising lipopeptide compounds or its salts.

Lipopeptide compounds, or pharmaceutically acceptable salts thereof, can be formulated for oral, intravenous, intramuscular, subcutaneous or parenteral administration for the therapeutic or prophylactic treatment of diseases, particularly bacterial infections. For oral or parenteral administration, lipopeptide compounds of this invention can be mixed with conventional pharmaceutical carriers and excipients and used in the form of tablets, capsules, elixirs, suspensions, syrups, wafers and the like. The compositions comprising a compound of this invention will contain from about 0.1 to about 99% by weight of the active compound, and more generally from about 10 to about 30%.

The pharmaceutical preparations disclosed herein are prepared in accordance with standard procedures and are administered at dosages that are selected to reduce, prevent or eliminate the infection (See, e. g., Remington's Pharmaceutical Sciences, Mack Publishing Company, Easton, Pa. and Goodman and Gilman's. The Pharmaceutical Basis of Therapeutics, Pergamon Press, New York, N.Y., the contents of which are incorporated herein by reference, for a general description of the methods for administering various antimicrobial agents for human therapy). The compositions of the invention (preferably of Formula I) can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. Nos. 4,452,775 (issued to Kent), 5,239,660 (issued to Leonard), 3,854,480 (issued to Zaffaroni).

The pharmaceuticallyacceptable compositions of the present invention comprise one or more compounds of the invention (preferably compounds of Formula I) in association with one or more non-toxic, pharmaceuticallyacceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral use, solid formulations such as tablets and capsules are particularly useful. Sustained release or enterically coated preparations may also be devised. For pediatric and geriatric applications, suspensions, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeuticallyeffective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl parahydroxybenzoate, propylene glycol, sorbitol, or sorbic acid.

For intravenous (IV) use, a lipopeptide compound according to the invention can be dissolved or suspended in any of the commonly used intravenous fluids and administered by infusion. Intravenous fluids include, without limitation, physiological saline or Ringer's solution. Intravenous administration may be accomplished by using, without limitation, syringe, minipump or intravenous line.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of a lipopeptide compound or a suitable soluble salt form of the compound, for example the hydrochloride salt, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular or parental formulation of a lipopeptide compound may be adminstered as a bolus or by slow infusion. A bolus is a dose that is administered in less than 30 minutes. In a preferred embodiment, a bolus is administered in less than 15 or less than 10 minutes. In a more preferred embodiment, a bolus is administered in less than 5 minutes. In an even more preferred embodiment, a bolus is administered in one minute or less. An infusion is a dose that is administered at a rate of 30 minutes or greater. In a preferred embodiment, the infusion is one hour or greater. In another embodiment, the infusion is substantially constant.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery. In another embodiment, the unit dosage form of the compound can be a solution of the compound or preferably a salt thereof in a suitable diluent in sterile, hermetically sealed ampoules or sterile syringes. The concentration of the compound in the unit dosage may vary, e.g. from about 1 percent to about 50 percent, depending on the compound used and its solubility and the dose desired by the physician. If the compositions contain dosage units, each dosage unit preferably contains from 1–500 mg of the active material. For adult human treatment, the dosage employed preferably ranges from 5 mg to 10 g, per day, depending on the route and frequency of administration.

In another aspect, the invention provides a method for inhibiting the growth of microorganisms, preferably bacteria, comprising contacting said organisms with a compound of the invention, preferably a compound of Formula I, under conditions which permit entry of the compound into said organism and into said microorganism. Such conditions are known to one skilled in the art and are exemplified in the Examples. This method involves contacting a microbial cell with a therapeutically-effective amount of compound(s) of the invention, preferably compound(s) of Formula I, in vivo or in vitro.

According to this aspect of the invention, the novel compositions disclosed herein are placed in a pharmaceutically acceptable carrier and are delivered to a recipient subject (preferably a human) in accordance with known methods of drug delivery. In general, the methods of the invention for delivering the compositions of the invention in vivo utilize art-recognized protocols for delivering the agent with the only substantial procedural modification being the substitution of the compounds of the invention (preferably compounds of Formula I) for the drugs in the art-recognized protocols Likewise, the methods for using the claimed composition for treating cells in culture, for example, to eliminate or reduce the level of bacterial contamination of a cell culture, utilize artrecognized protocols for treating cell cultures with antibacterial agent(s) with the only substantial procedural modification being the substitution of the compounds of the invention (preferably compounds of Formula I) for the agents used in the art-recognized protocols.

In one embodiment, the invention provides a method for treating an infection, especially those caused by gram-positive bacteria, in a subject with a therapeutically-effective amount of a lipopeptide compound according to Formula I. Exemplary procedures for delivering an antibacterial agent are described in U.S. Pat No. 5,041,567, issued to Rogers and in PCT patent application number EP94/02552 (publication no WO 95/05384), the entire contents of which documents are incorporated in their entirety herein by reference. As used herein the phrase "therapeutically-effective amount" means an amount of a compound of the present invention that prevents the onset, alleviates the symptoms, or stops the progression of a bacterial infection. The term "treating" is defined as administering, to a subject, a therapeutically-effective amount of a compound of the invention (preferably a compound of Formula I) both to prevent the occurrence of an infection and to control or eliminate an infection. The term "subject", as described herein, is defined as a mammal, a plant or a cell culture. In a preferred embodiment, a subject is a human or other animal patient in need of lipopeptide compound treatment.

The method comprises administering to the subject an effective dose of a compound of this invention. An effective dose is generally between about 0.1 and about 100 mg/kg of a lipopeptide compound of Formula I or a pharmaceutically acceptable salt thereof. A preferred dose is from about 0.1 to about 50 mg/kg of a lipopeptide compound of Formula I or a pharmaceutically acceptable salt thereof. A more preferred dose is from about 1 to 25 mg/kg of a lipopeptide compound of Formula I or a pharmaceutically acceptable salt thereof An effective dose for cell culture is usually between 0.1 and 1000 $\mu$g/mL, more preferably between 0.1 and 200 $\mu$g/mL.

The compound of Formula I can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound and the microorganism or microorganisms involved in the infection. A method of administration to a patient of daptomycin, another member of the lipopeptide compound class is disclosed in U.S. Ser. No. 09/406,568, filed Sep. 24, 1999, which claims the benefit of U.S. Provisional Application Ser. Nos. 60/101,828, filed Sep. 25, 1998, and 60/125,750, filed Mar. 24, 1999.

A lipopeptide compound according to this invention may also be administered in the diet or feed of a patient or animal. If administered as part of a total dietary intake, the amount of compound employed can be less than 1% by weight of the diet and preferably no more than 0.5% by weight. The diet for animals can be normal foodstuffs to which the compound can be added or it can be added to a premix.

The methods of the present invention comprise administering a lipopeptide compound of Formula I or a pharmaceutical composition thereof to a subject in need thereof in an amount that is efficacious in reducing or eliminating the bacterial infection. The compound may be administered orally, parenterally, by inhalation, topically, rectally, nasally, buccally, vaginally, or by an implanted reservoir, external pump or catheter. The compound may be prepared for opthalmic or aerosolized uses. The compounds of the present invention can be administered as an aerosol for the treatment of pneumonia or other lung-based infections. A preferred aerosol delivery vehicle is an anhydrous or dry powder inhaler. Lipopeptide compounds of Formula I or a pharmaceutical composition thereof also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In a preferred embodiment, lipopeptide compounds are administered intravenously, subcutaneously or orally. In a preferred embodiment for administering a lipopeptide compound according to Formula I to a cell culture, the compound may be administered in a nutrient medium.

The method of the instant invention may be used to treat a subject having a bacterial infection in which the infection is caused or exacerbated by any type of bacteria, particularly gram-positive bacteria. In one embodiment, a lipopeptide compound or a pharmaceutical composition thereof is administered to a patient according to the methods of this invention. In a preferred embodiment, the bacterial infection may be caused or exacerbated by gram-positive bacteria. These gram-positive bacteria include, but are not limited to, methicillin-susceptible and methicillin-resistant staphylococci (including *Staphylococcus aureus, S. epidermidis, S. haemolyticus, S. hominis, S. saprophyticus*, and coagulase-negative *staphylococci*), glycopeptide intermediary-susceptible *S. aureus* (GISA), penicillin-susceptible and penicillin-resistant *streptococci* (including *Streptococcus pneumoniae, S. pyogenes, S. agalactiae, S. avium, S. bovis, S. lactis, S. sangius* and *Streptococci* Group C, *Streptococci* Group G and viridans *streptococci*), enterococci (including vancomycin susceptible and vancomycin-resistant strains such as *Enterococcusfaecalis* and *E. faecium*), *Clostridium difficile, C. clostridiiforme, C. innocuum, C. perfringens, C. ramosum, Haemophilus influenzae, Listeria monocytogenes, Corynebacterium jeikeium, Bifidobacterium* spp., *Eubacterium aerofaciens, E. lentum, Lactobacillus acidophilus, L. casei, L. plantarum, Lactococcus* spp., *Leuconostoc* spp., *Pediococcus, Peptostreptococcus anaerobius, P. asaccarolyticus, P. magnus, P. micros, P. prevotil, P. productus, Propionibacterium acnes, Actinomyces* spp., *Moraxella* spp. (including *M. catarrhalis*) and *Escherichia* spp. (including *E. coli*).

In a preferred embodiment, the antibacterial activity of lipopeptide compounds of Formula I against classically "resistant" strains is comparable to that against classically "susceptible" strains in in vitro experiments. In another preferred embodiment, the minimum inhibitory concentration (MIC) value for lipopeptide compounds according to this invention against susceptible strains is typically the same or lower than that of vancomycin. Thus, in a preferred embodiment, a lipopeptide compound of this invention or a pharmaceutical composition thereof is administered according to the methods of this invention to a patient who exhibits a bacterial infection that is resistant to other compounds, including vancomycin or daptomycin. In addition, unlike glycopeptide antibiotics, lipopeptide compounds exhibits rapid, concentrationdependent bactericidal activity against gram-positive organisms. Thus, in a preferred embodiment, a lipopeptide compound according to this invention or a pharmaceutical composition thereof is administered according to the methods of this invention to a patient in need of rapidly acting antibiotic therapy.

The method of the instant invention may be used for any bacterial infection of any organ or tissue in the body. In a preferred embodiment, the bacterial infection is caused by gram-positive bacteria. These organs or tissue include, without limitation, skeletal muscle, skin, bloodstream, kidneys, heart, lung and bone. The method of the invention may be used to treat, without limitation, skin and soft tissue infections, bacteremia and urinary tract infections The method of the invention may be used to treat community acquired respiratory infections, including, without limitation, otitis media, sinusitis, chronic bronchitis and pneumonia, including pneumonia caused by drug-resistant *S. pneumoniae* or *H. influenzae*. The method of the invention also may be used to treat mixed infections that comprise different types of gram-positive bacteria, or which comprise both gram-positive and gram-negative bacteria. These types of infections include intra-abdominal infections and obstetrical/gynecological infections. The method of the invention also may be used to treat an infection including, without limitation, endocarditis, nephritis, septic arthritis, intra-abdominal sepsis, bone and joint infections. and osteomyelitis. In a preferred embodiment, any of the above-described diseases may be treated using lipopeptide compounds according to this invention or pharmaceutical compositions thereof.

The method of the instant invention may also be practiced while concurrently administering one or more other antimicrobial agents, such as antibacterial agents (antibiotics) or antifungal agents. In one aspect, the method may be practiced by administering more than one lipopeptide compounds according to this invention. In another embodiment, the method may be practiced by administering a lipopeptide compound according to this invention with another lipopeptide compound, such as daptomycin.

Antibacterial agents and classes thereof that may be co-administered with a compound of the present invention include, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomicin, glycopeptide, glycylcycline, ketolides, oxazolidinone; imipenen, amikacin, netilmicin, fosfomycin, gentamicin, ceftriaxone, Ziracin, LY 333328, CL 331002, Linezolid, Synercid, Aztreonam, Metronidazole, Epiroprim, OCA-983, GV-143253, Sanfetrinem sodium, CS-834, Biapenem, A-99058.1, A-165600, A-179796, KA 159, Dynemicin A, DX8739, DU 6681; Ceflupranem, ER 35786, Cefoselis, Sanfetrinem celexetil, HGP-31, Cefpirome, HMR-3647, RU-59863, Mersacidin, KP 736, Rifalazil; Kosan, AM 1732, MEN 10700, Lenapenem, BO 2502A, NE-1530, PR 39, (L-arginyl-L-ariginyl-L-arginyl-L-prolyl-L-arginyl-L-prolyl-L-prolyl-L-tryosyl-L-leucyl-L-prolyl-L-arginyl-L- prolyl-L-arginyl-L-prolyl-L-prolyl-L-prolyl-L-phenylalanyl-L-phenylalanyl-L-prolyl-L-prolyl-L-arginyl-L-leucyl-L-prolyl-L-prolyl-L-arginyl-L-isoleucyl-L-prolyl-L-prolylglycyl-L-phenylalanyl-L-prolyl-L-prolyl-L-arginyl-L-phenylalanyl-L-prolyl-L-prolyl-L-arginyl-L-phenylalanyl-L-prolinamide [SEQ. ID NO: 1]), K130, OPC 20000, OPC 2045, Veneprim, PD 138312, PD 140248, CP 111905, Sulopenem, ritipenam acoxyl, RO-65-5788, Cyclothialidine, Sch-40832, SEP-132613, micacocidin A, SB-275833, SR-15402, SUN A0026, TOC 39, carumonam, Cefozopran, Cefetamct pivoxil, and T 3811.

In a preferred embodiment, antibacterial agents that may be co-administered with a compound according to this invention include, without limitation, imipenen, amikacin, netilmicin, fosfomycin, gentamicin, ceftriaxone, teicoplanin, Ziracin, LY 333328, CL 331002, R 3647, Linezolid, Synercid, Aztreonam, and Metronidazole.

Antifungal agents that may be co-administered with a compound according to this invention include, without limitation, Caspofungen, Voriconazole, Sertaconazole, IB-367, FK-463, LY-303366, Sch-56592, Sitafloxacin, DB-289 polyenes, such as Amphotericin, Nystatin, Primaricin; azoles, such as Fluconazole, Itraconazole, and Ketoconazole; allylamines, such as Naftifine and Terbinafine; and anti-metabolites such as Flucytosine. Other antifungal agents include without limitation, those disclosed in Fostel et al., Drug Discovery Today 5:25–32 (2000), herein incorporated by reference. Fostel et al. disclose antifungal compounds including Corynecandin, Mer-WF3010, Fusacandins, Artrichitin/LL 15G256γ, Sordarins, Cispentacin, Azoxybacillin, Aureobasidin and Khafrefungin.

Lipopeptide compounds may be administered according to this method until the bacterial infection is eradicated or reduced. In one embodiment, a lipopeptide compound is administered for a period of time from 3 days to 6 months. In a preferred embodiment, a lipopeptide compound is administered for 7 to 56 days. In a more preferred embodiment, a lipopeptide compound is administered for 7 to 28 days. In an even more preferred embodiment, a lipopeptide compound is administered for 7 to 14 days. Lipopeptide compounds may be administered for a longer or shorter time period if it is so desired.

General Procedures for Lipopeptide Compound Synthesis

Lipopeptide compounds of Formula I may be produced as described below. The lipopeptide compounds of the instant invention may be produced semi-synthetically using daptomycin as a starting point or may be produced by a total synthesis approach.

For the semi-synthetic approach according to the present invention, daptomycin may be prepared by any method known in the art. See, e.g., U.S. Pat. Nos. 4,885,243 and 4,874,843. Daptomycin may be used in its acylated state or it may be deacylated prior to its use as described herein. Daptomycin may be deacylated using *Actinoplanes utahensis* as described in U.S. Pat. No. 4,482,487. Alternatively, daptomycin may be deacylated as follows:

Daptomycin (5.0 g) was dissolved in water (25 ml) and adjusted to pH 9 with 5M sodium hydroxide. Ditertbutyldicarbonate (1.5 g) was added and the mixture was adjusted to maintain pH 9 with 5 M sodium hydroxide until the reaction was complete (4 hours). The pH was adjusted to 7 and the mixture was loaded onto a Bondesil 40μ C8 resin column. The column was washed with water and the product was eluted from the column with methanol. Evaporation of the methanol gave BOC-protected daptomycin as a yellow powder.

A preparation of deacylase enzyme was produced from recombinant *Streptomyces lividans*, which expresses the *Actinoplanes utahensis* deacylase enzyme. The enzyme in ethylene glycol (400 μl) was added to BOC-protected daptomycin (1 g) in water (100 ml) at pH 7–8. After incubation for 72 hours, the mixture was loaded on a Bondesil 40μ C8 resin column. The column was washed with water and the product was eluted from the column with 10% acetonitrile in water. The product was evaporated to give deacylated BOC-protected daptomycin as a yellow powder Kynurenine Derivatives Scheme 1

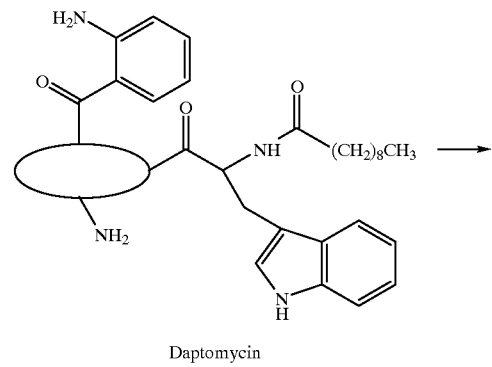

Daptomycin

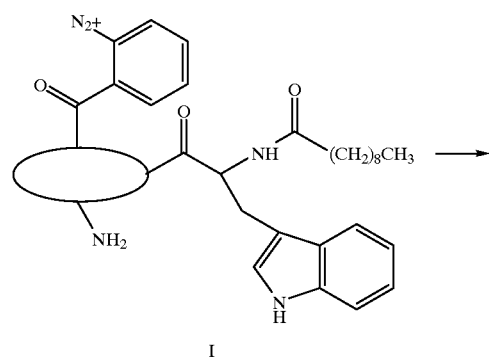

I

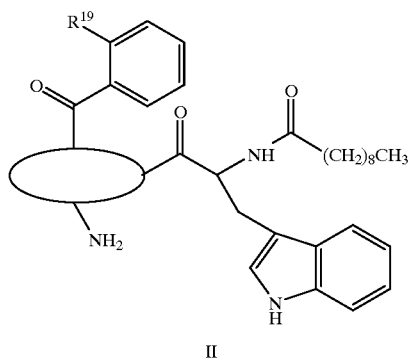

II

Daptomycin can be converted into analogs bearing modifications at the $R^2$ position by converting the aromatic amino group to the diazonium salt compound I with reagents such as sodium nitrite/hydrochloric acid or isoamylnitrite. Using chemistry known to those skilled in the art and following the teachings of the disclosure, the diazonium group can then be displaced by reagents such as sodium azide, potassium ethylxanthate or copper chloride to yield derivative compounds II, wherein $R^{19}$ is as previously defined.

Additionally, compound I can be converted to the azide compound III by reaction with an azide source, typically sodium azide. Modifications to the ketone group can then be undertaken using chemistry known to those having ordinary skill in the art, such as reduction, oxime formation, ketalization conversion to a leaving group and displacement to give compounds of formula IV, wherein $R^{17}$ and $R^{18}$ are as previously defined.

Scheme 2

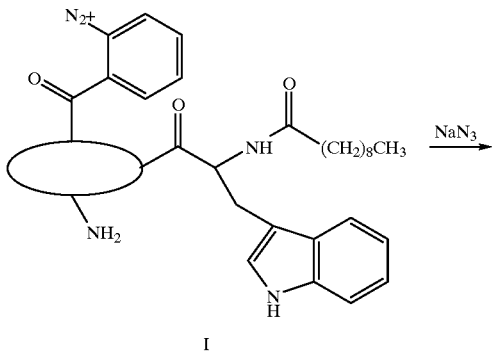

I

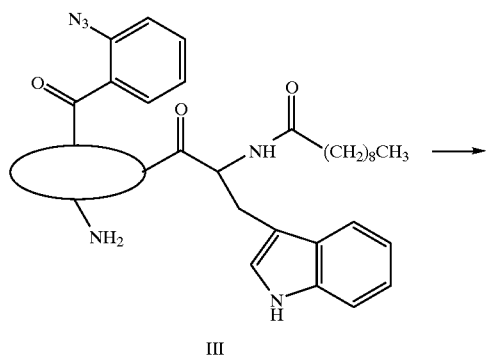

III

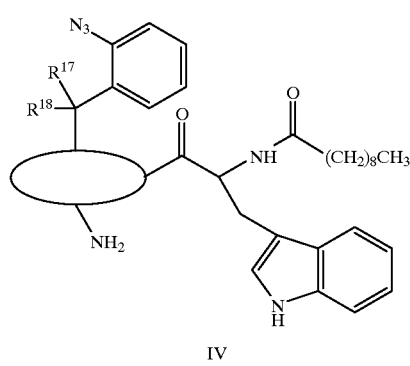

IV

Scheme 3

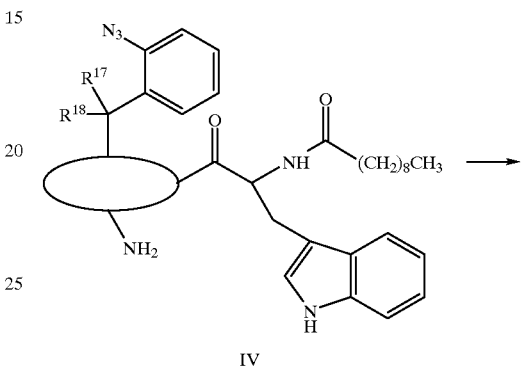

IV

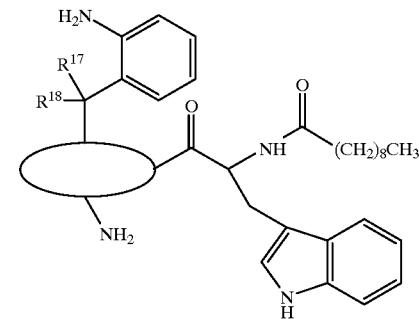

V

Compound IV may also be converted to compound V by reducing the azide group to the amine using chemistry known to those having ordinary skill in the art, and following the teachings of the disclosure, such as reaction with triphenyl phosphine and water, or reducing agents such as sodium borohydride wherein $R^{17}$ and $R^{18}$ are as previously defined.

Scheme 4

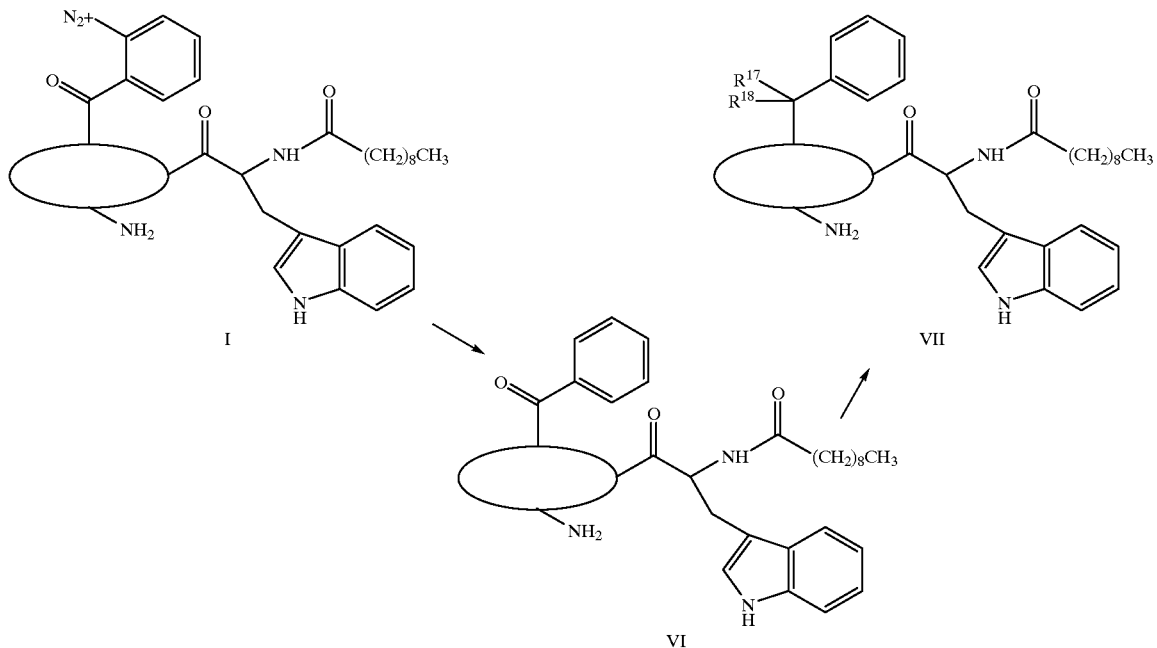

Additionally compound I can be converted into compound VI by reduction with hypophosphorus acid. Modifications to the ketone group can then be undertaken using chemistry known to those having ordinary skill in the art similar to those used in scheme 2, wherein $R^{17}$ and $R^{18}$ are as previously defined.

Ornithine Derivatives

Daptomycin can be converted into analogs bearing modifications at the $R^1$ position by treating the amino group of the ornithine with reagents such as isocyanates, isothiocyanates, activated esters, acid chlorides, sulfonylchlorides or activated sulfonamides, heterocycles bearing readily displaceable groups, imidates, lactones or reductively with aldehydes to yield compound VIII, wherein $R^1$ is as previously defined.

Tryptophan Amine Derivatives

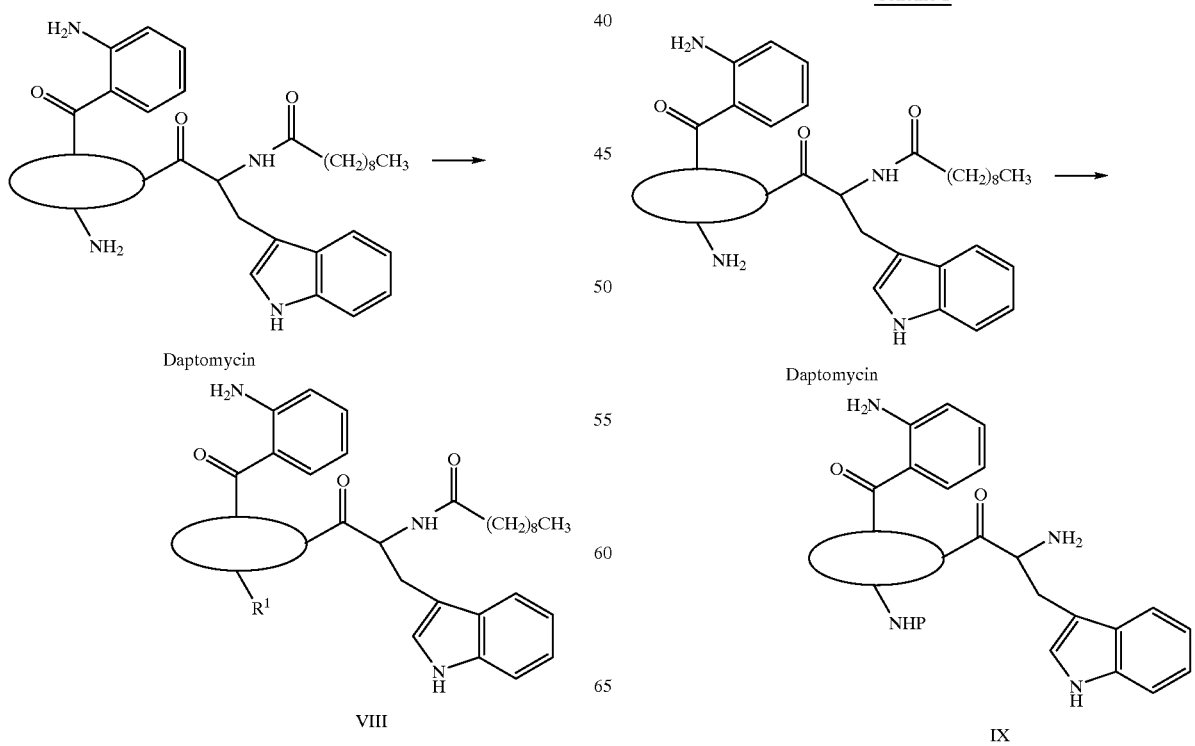

Daptomycin can be converted into compound IX by first protecting the ornithine amine with an appropriate amino protecting group (P) known to those skilled in the art and following the teachings of the disclosure. The decyl side chain on the tryptophan is then removed using an enzyme capable of deacylating daptomycin, such as that described above.

Scheme 2

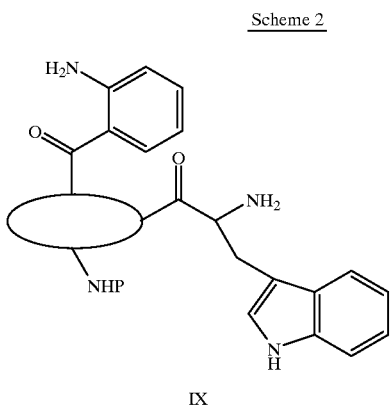

IX

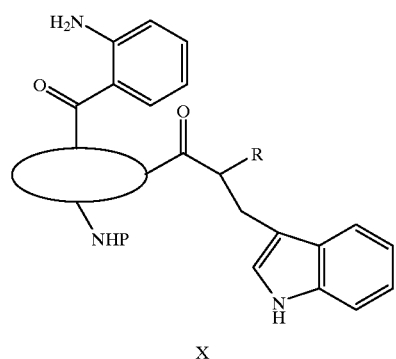

X

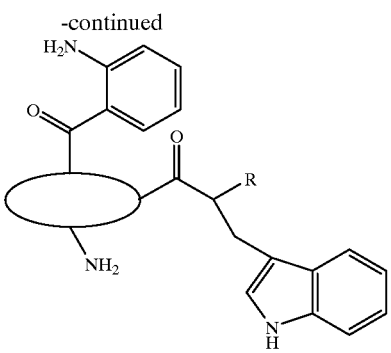

XI

Compound IX can be modified at the tryptophan amine with reagents such as isocyanates, isothiocyanates, activated esters, acid chlorides, sulfonylchlorides or activated sulfonamides, heterocycles bearing readily displaceable groups, imidates, lactones or reductively with aldehydes to yield compound X. Compound X can be deprotected to give compound XI according to procedures known to those skilled in the art following the disclosure of this invention, wherein R is as previously defined.

The above modifications to the ornithine amine $R^1$, tryptophan amine R or kynurenine side chain $R^2$ may be independently combined to yield additional compounds that are modified at up to all three sites. In order to achieve these modifications, it may be necessary to protect certain functionalities in the molecule. Protecting these functionalities should be within the expertise of one skilled in the art following the disclosure of this invention. See, e.g., Greene, supra.

Solid Support Synthesis of Lipopeptide Compounds

In an alternative embodiment of the invention, the lipopeptide compounds of Formula I may be synthesized on a solid support as outlined below. In step 1, a suitably N-protected-βMeGlu(OH)—OAllyl ester is coupled to a suitable resin to give Compound XII. Deprotection of the amino group of Compound XII, followed by coupling of the amino group with a suitably protected seryl derivative (Al) gives Compound XIII, wherein P is a suitable protecting group. This peptide coupling process, i.e., deprotection of the alpha-amino group, followed by coupling to a suitably protected amino acid, is repeated until the desired number of amino acids have been coupled to the resin. In the scheme shown below, eleven amino acids have been coupled to give Compound XIV. Addition of an activated R group, R*, is added to Compound XIV to give Compound XV. In step 4, Compound XV is cyclized to give Compound XVI. Subsequently, in step 5, Compound XVI is removed from the resin to give the lipopeptide Compound XVII.

Synthetic Scheme for Total Synthesis of Lipopeptide Compounds

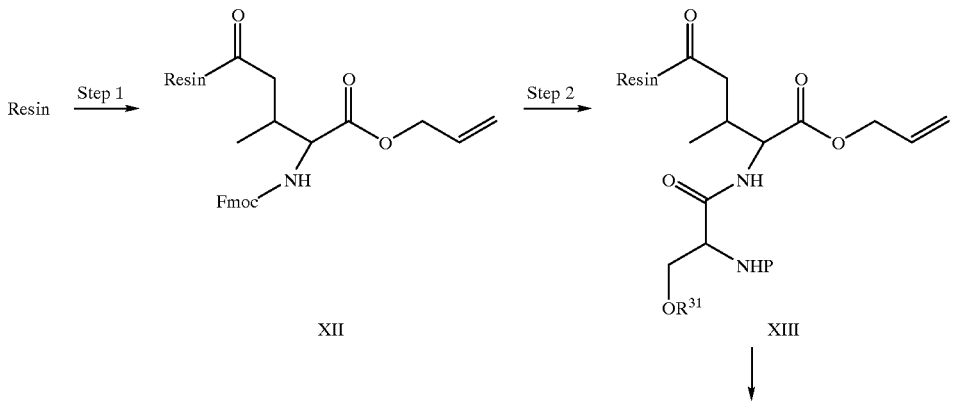

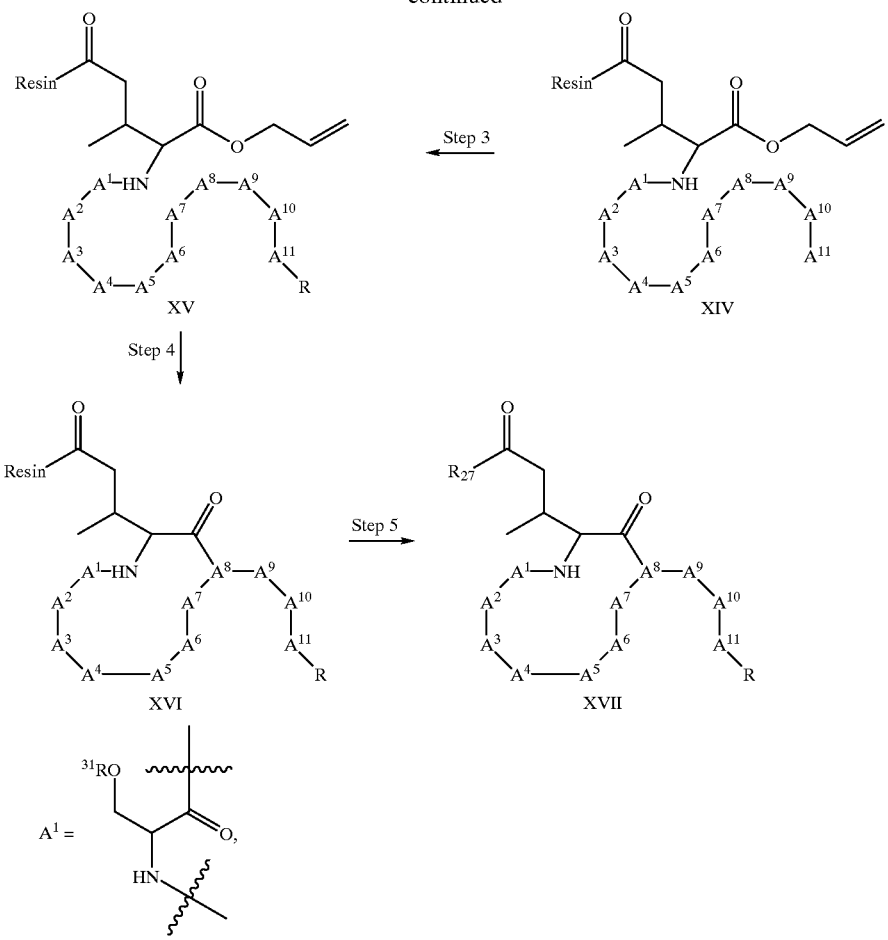

wherein $A^1$, is a suitably protected serine derivative, wherein $R^{31}$ is a suitable, cleavable hydroxyl protecting group as outlined below.

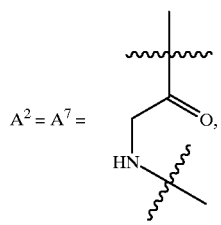

wherein $A^2$ and $A^7$, are suitably protected glycine derivatives as outlined below.

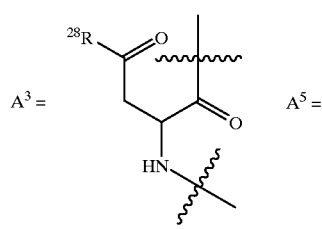

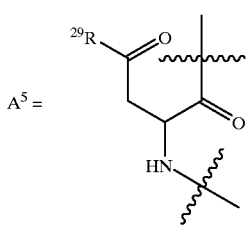

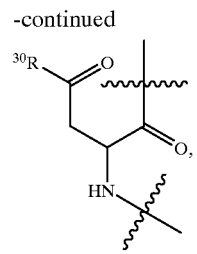

wherein $A^3$, $A^5$ and $A^9$ are suitably protected aspartic acid derivatives as outlined below, wherein $^{28}R$, $^{29}R$ and $^{30}R$ are cleavable protecting groups, preferably t-butyl groups.

wherein $A^4$ is a suitably protected alanine derivative as outlined below.

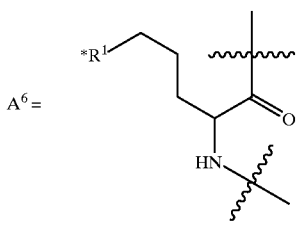

wherein $A^6$ is a suitably protected ornithine derivative as outlined below, or derivatized ornthine wherein $*R^1$ is $R^1$ as previously described or alternatively a protected form of $R^1$ that would yield $R^1$ upon subsequent deprotection.

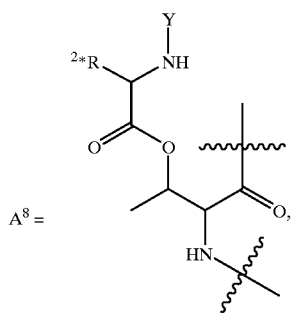

wherein $A^8$ is a suitably protected depsipeptide as outlined below, Y is a protecting group that is cleavable under conditions that leave other protecting groups intact to the others used, i.e., Alloc; and wherein $*R^2$ is $R^2$ as previously described or alternatively a protected form of $R^2$ that would yield $R^2$ upon subsequent deprotection. Preferably $^{2*}R$ is a kynurenine, or substituted kynurenine side chain, most preferably

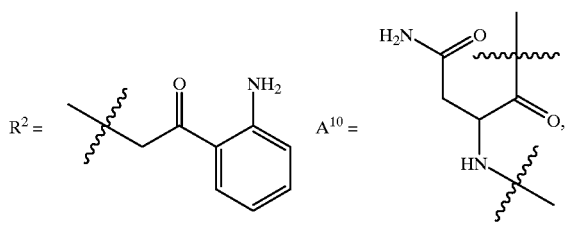

wherein $A^{10}$ is a suitably protected asparagine derivative as outlined below.

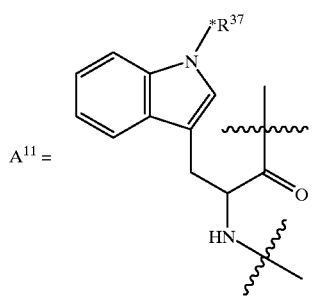

wherein $A^{11}$ is a suitably protected tryptophan derivative as koutlined below, wherein $R^{*37}$ is hydrido or a suitable protecting group, preferably t-butoxy carbonyl.

It will be understood by those skilled in the art that both the amino and the side chain functional groups must be suitably protected prior to attaching them to the growing peptide chain. Suitable protecting groups can be any group known in the art to be useful in peptide synthesis. Such pairings of protecting groups are well known See, e.g., "Synthesis Notes" in the Novabiochem Catalog and Peptide Synthesis Handbook (1999), pages S1–S93 and references cited therein. Following the disclosure of the present application, the selection of protecting groups and method of use thereof will be known to one skilled in the art.

It will also be understood by those skilled in the art that the choice of protecting group on the side chain functional groups will either result or not result in the protecting group being cleaved concomitantly with the peptide's final cleavage from the resin, which will give the natural amino acid functionality or a protected derivative thereof, respectively.

The following general procedures serve to exemplify the solid support synthesis of compounds of Formula I.

Step 1: Coupling Suitably-N-protected,β-MeGlu(OH)—OAllyl Ester to a Resin

Five molar equivalents each, with respect to the resin, of a suitably-N-protectedβMeGlu(OH)—OAllyl ester, 1,3-Diisopropylcarbodiimide (DIC) and 1-Hydroxy-7-azabenzotriazole (HOAt) are stirred for 30 mins in dimethylformamide (DMF; 5 ml/g resin). A suitably functionalised resin or solid support, such as, but not limited to, Wang, Safety Catch, Rink, Knorr, PAL, or PAM resin, is added and the resulting suspension is stirred for 16 hrs. The resin-N-protected βMeGlu(OH)—OAllyl ester is then filtered, dried and the coupling is repeated. The N-protecting group is then removed using the appropriate conditions given in the coupling steps below.

Step 2: (A) General Coupling Cycle for Amino Acids with an N-9-Fluorenylmethoxycarbonyl (Fmoc) Protecting Group Five molar equivalents each, with respect to the resin-AA(wherein resin-AA is defined as the resin attached the the growing amino acid chain), of a suitably protected Fmoc amino acid, DIC, and HOAt (0.5 molar solution in DMF) are added to the resin-AA, along with sufficient DMF to give a working volume. The mixture is shaken for one hour, filtered, and the coupling is repeated. After the second coupling the resin is washed twice with DMF, twice with methanol, and twice again with DMF. The Fmoc group of the newly coupled amino acid $A^{1-11}$ is deprotected by stirring the resin product in one working volume of a solution of 20% piperidine in N-methyl pyrolidine for five minutes, filtering the resin, and stirring the resin in 20% piperidine in N-methyl pyrolidine again for 20 minutes. The resin is washed twice with DMF, twice with methanol, and twice again with DMF.

Step 2 (B): General Coupling Cycle of Amino Acids with an N-tert-Butoxycarbonyl (N-Boc) Protecting Group Five molar equivalents each, with respect to the resin-AA, of a suitably protected N-Boc amino acid, DIC, and HOAt (0.5 molar solution in DMF) are added to the resin-AA, along with sufficient DMF to give a working volume. The mixture is shaken for one hour, filtered, and the coupling is repeated. After the repeated coupling the resin is washed twice with DMF, twice with methanol, and twice again with DMF. The Boc group of the newly coupled amino acid $A^{1-11}$, is then deprotected by stirring the resin in one working volume of $CH_2Cl_2$:trifluoroacetic acid (TFA) 1:1 for 15 minutes, filtering, and stirring in one working volume of $CH_2Cl_2$:TFA 1:1 for another 15 minutes. The resin is neutralized by washing with excess diisopropylethylamine (DIPEA) in $CH_2Cl_2$ and then washed twice with DMF, twice with methanol, and twice again with DMF.

Step 3: Terminal Amine Capping Reaction

Ten molar equivalents, with respect to the resin XV, of a suitable reagent containing R* such as an activated ester, isocyanate, thioisocyanate, anhydride, acid chloride, chloroformate, or reactive salt thereof, in one working volume of DMF is added to the resin XIV and agitated for 25 hours. The resulting resin XV is washed twice with DMF, twice with methanol, and twice again with DMF.

Step 4: Cyclization

The dried resin XV is placed under an argon atmosphere, and treated with a solution of $Pd(PPh_3)_4$ 125 mgs/0.1 mmol peptide substrate, in $CH_2Cl_2$: Acetic acid: N-Methylmorpholine, 40:2:1, 1 ml/0.1 mmol peptide substrate. The mixture is stirred for 3 hours at ambient temperature, filtered, and washed twice with DMF, twice with methanol, and twice again with DMF. Five molar equivalents each, with respect to the resin, of DIC, and HOAt (0.5 molar solution in DMF) are added to the resin, along with sufficient DMF to give a working volume. The reaction is shaken for 17 hours, filtered, and washed twice with DMF, twice with methanol, and twice again with DMF to give resin XVI.

Step 5: Cleavage and Isolation of the Lipopeptide

The desired lipopeptide is cleaved from resin XVI and isolated, resulting in a compound in which $R^{27}$ is OH or $NH_2$. If Fmoc chemistry is used, the dried resin is suspended in 1 ml/0.1 mmol peptide substrate of $CH_2Cl_2$:TFA:Ethanedithiol (EDT):Triusopropylsilane (TIS), 16:22:1:1, and stirred for 6–8 hours at ambient temperature. The resin is filtered, washed with 1 equal volume of cold TFA, and the combined filtrates are evaporated under reduced pressure. Crude product XVII is then precipitated by the addition of diethyl ether, and isolated by centrifugation. This product may be further purified by preparative reverse phase HPLC.

If N-Boc chemistry is used, the dried resin is suspended in hydrogen flouride (HF):anisole:dimethylsulfide (DMS), 10:1:1, and stirred for 2 hours at 0° C. The volitiles are evaporated under a stream of nitrogen. The resin is then extracted with TFA, filtered and washed twice with TFA, and the combined TFA filtrates evaporated under reduced pressure. Crude product is then precipitated by the addition of diethyl ether, and isolated by centrifugation. This product may be further purified by preparative reverse phase HPLC.

If the resin is a Safety Catch resin, then $R^{27}$=OR or NRH. The dried resin XVI is suspended in N-methylpyrolidine (No) or dimethylsulphoxide (DMSO) (8 ml/g resin), Five equivalents of DIPEA (with respect to resin substitution) and 24 equivalents of iodo or bromoacetonitrile (with respect to resin substitution) are added. The suspension is stirred for 24 hours at ambient temperature under inert atmosphere. The resin is filtered, washed with tetrahydrofuran (THF) and DMSO. For an ester, the resin is then treated with an alcohol, hydroxide or alkoxide (20 equivalents with respect to resin substitution) in THF for 20 hours. The resin is filtered, washed with THF and water, and the combined filtrates are evaporated under reduced pressure. Crude product is precipitated by the addition of diethyl ether, and isolated by centrifugation. The product may be further purified by preparative reverse phase HPLC. For amides the resin is then treated with a primary or secondary amine (20 equivalents with respect to resin substitution) in THF for 12–40 hours, at a gentle reflux under inert atmosphere. The resin is filtered, washed with THF and water, and the combined filtrates are evaporated under reduced pressure. Crude product is then precipitated by the addition of diethyl ether, and isolated by centrifugation. This product may be further purified by preparative reverse phase HPLC.

In order that this invention may be more fully understood, the following examples are set forth. These examples are for the purpose of illustration only and are not to be construed as limiting the scope of the invention in any way.

EXAMPLE 1

Preparation of Compounds 1, 19, 40–44, 49, 72–74, 100, 115–116 and 123–125

Daptomycin (5.0 g) was dissolved in water (25 ml) and adjusted to pH 9 with 5M sodium hydroxide. Ditertbutyl-dicarbonate (1.5 g) was added and the mixture was adjusted to maintain pH 9 with 5 M sodium hydroxide until the reaction was complete (4 hours). The pH was adjusted to 7 and the mixture was loaded onto a Bondesil 40μ C8 resin column. The column was washed with water and the product was eluted from the column with methanol. Evaporation of the methanol gave BOC-protected daptomycin (5.08 g) as a yellow powder.

A preparation of deacylase enzyme was produced from recombinant *Streptomyces lividans*, which expresses the *Actinoplanes utahensis* deacylase enzyme. The enzyme in ethylene glycol (400 μl) was added to BOC-protected daptomycin (1 g) in water (100 ml) at pH 7–8. After incubation for 72 hours, the mixture was loaded on a Bondesil 40μ C8 resin column. The column was washed with water and the product was eluted from the column with 10% acetonitrile in water. The product was evaporated to give deacylated BOC-protected daptomycin (440 mg) as a yellow powder.

Deacylated BOC-protected daptomycin (100 mg) and octyl isocyanate (20 μl) were stirred at room temperature in dry dimethylformamide (5 ml) for 24 hours. Evaporation of the solvent gave a yellow powder residue, which was stirred in a mixture of trifluoroacetic acid/dichloromethane/triisopropylsilane/ethane dithiol (11/8/0.5/0.5) (2 ml) for 2 hours. Evaporation gave a yellow residue that was purified by preparative HPLC on an IBSILC-8 5μ 250×20.2 mm column. The column was eluted at 20 ml/min with 36% acetonitrile in 5 mM ammonium phosphate buffer. Collected fractions were freeze-dried. The freeze-dried residue was dissolved in water (5 ml) and applied to a Bondesil 40μ C8 resin column. The column was washed with water and eluted with methanol. Evaporation of the methanol gave compound 1 as a pale yellow solid (30 mg).

In an analogous manner, compounds 19, 40–44, 49, 72–74, 100, 115–116 and 123–125 can be prepared by those having ordinary skill in the art following the teachings of the disclosure as detailed in the above example by appropriate substitutions of reagents.

EXAMPLE 1a

Preparation of Compounds 18, 37–39, 45–47

Deacylated BOC-protected daptomycin (100 mg) and 4-chloro-4-biphenyl acetic acid pentafluorophenyl ester (32 mg) were stirred in dry dimethylformamide (3 ml) at room temperature for two days. The mixture was loaded on an IBSIL-C8 5μ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40μ C8 resin column, washed with water and eluted with methanol. Evaporation of the methanol gave the Boc-protected intermediate as a pale yellow solid (41 mg).

The Boc-protected intermediate (40 mg) was stirred in trifluoroacetic acid (2 ml) and anisole (0.1 ml) at room temperature for 2 hours. Removal of the solvents under reduced pressure gave a residue which was loaded onto an IBSIL-C8 5μ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40μ C8 resin column, washed with water and eluted with methanol. Evaporation of the methanol gave compound 18 as a pale yellow solid (10 mg).

In an analogous manner, compounds 37–39 and 45–47 can be prepared by those having ordinary skill in the art following the teachings of the disclosure as detailed abovein the above example by appropriate substitution of reagents.

EXAMPLE 1b

Preparation of Compounds 110, 112, 109 and 111

Boc-protected daptomycin α,β-tridecenoyl amide (compound 110) was prepared from deacylated Boc-protected daptomycin α,β-tridecenoyl pentafluorophenol ester according to Examples 1 and 1a. Compound 110 (0.21 g) in dry dichloromethane (8 ml), trifluoroacetic acid (11 ml) and ethane dithiol (0.25 ml) was stirred for 3 hours at room temperature. Concentration under reduced pressure gave a light brown oil which was purified on an IBSIL-C8 5μ 250×20.2 mm column and eluted at 25 ml/min with 30–60% acetonitrile in 5 mM ammonium phosphate gradient over 40 minutes. Fractions containing the desired compound were collected and freeze-dried. The freeze-dried residue was dissolved in water (5 ml) and applied to a Bondesil 40μ C8 resin column, washed with water and eluted with methanol. Evaporation of the methanol gave compound 112 (53.8 mg) as a pale yellow solid.

In an analogous manner, compounds 109 and 111 can be prepared by those having ordinary skill in the art following the teachings of the disclosure as detailed abovein the above example by appropriate substitution of reagents.

EXAMPLE 2

Preparation of Compound 2

Dodecyl isocyanate (0.507 g) in dry dimethylformamide (3 ml) was added to deacylated Boc-protected daptomycin (3.14 g) in dry dimethylformamide (30 ml). The mixture was stirred at room temperature under nitrogen. After 7 hours the mixture was purified on a Bondesil 40μ C8 resin column with 10% acetonitrilewater followed by 50% acetonitrile-water. The desired fractions were freeze-dried to give Boc-protected daptomycin dodecyl urea (3.38 g) as pale yellow fluffy solid.

Boc-protected daptomycin dodecyl urea (2.42 g) in dry dichloromethane (20 ml), trifluoroacetic acid (22 ml) and ethane dithiol (0.5 ml) was stirred for 4 hours at room temperature. The mixture was concentrated to a light brown oil then triturated with methanol and diethyl ether. After the mixture was centrifuged the yellow residue was loaded on an IBSIL-C8 5μ 250×20.2 mm column and eluted at 25 ml/min with 30–60% acetonitrile in 5 mM ammonium phosphate gradient over 40 minutes. Fractions containing the desired compound were collected and freeze-dried. The freeze-dried residue was dissolved in water (5 ml) and applied to a Bondesil 40μ C8 resin column, washed with water and eluted with methanol. Evaporation of the methanol gave compound 2 (2.53 g) as pale yellow solid.

EXAMPLE 2a

Preparation of Compound 48

Undecyl isocyanate (0.197 g) in dry dimethylformamide (1 ml) was added to deacylated Boc-protected daptomycin (1.62 g) in dry dimethylformamide (20 ml). The mixture was stirred at room temperature under nitrogen for 7 hours. The mixture was then purified on a Bondesil 40μ C8 resin column with 10% acetonitrile water followed by 50% acetonitrilewater. The desired fractions were freeze-dried to give Boc-protected daptomycin undecyl urea (1.58 g) as pale yellow fluffy solid.

Boc-protected daptomycin undecyl urea (1.58 g) in dry dichloromethane (20 ml), trifluoroacetic acid (22 ml) and 5% anisole was stirred for 4 hours before being evaporated to dryness. The residue was loaded on an IBSIL-C8 5μ 250×20.2 mm column and eluted at 25 ml/min with 30–60% acetonitrile in 5 mM ammonium phosphate gradient over 40 minutes. Fractions containing the desired compound were collected and freeze-dried. The freeze-dried residue was dissolved in water (5 ml) and applied to a Bondesil 40μ C8 resin column, washed with water and eluted with methanol. Evaporation of the methanol gave compound 48 (136.5 mg) as pale yellow solid.

EXAMPLE 2b

Preparation of compounds 117 and 118

Nonyl isocyanate (40.6 mg) in dry dimethylformamide (0.2 ml) was added to deacylated Boc-protected daptomycin (313.2 mg) in dry dimethylformamide (2ml) The mixture was stirred at room temperature under nitrogen. After 7 hours the mixture was purified on an IBSIL-C8 5μ 250×20.2 mm column and eluted at 25 ml/min with 30–60% acetonitrile in 5 mM ammonium phosphate gradient over 40 minutes. Fractions containing the desired compound were collected at 21 minutes and freeze-dried. The freeze-dried residue was dissolved in water (5 ml) and applied to a Bondesil 40μ C8 resin column, washed with water and eluted with methanol. Evaporation of the methanol gave compound 117 (158.8 mg) as pale yellow solid.

Compound 117 (58.9 mg) in dry dichloromethane (5 ml), trifluoroacetic acid (2 ml) and ethane dithiol (0.05 ml). The mixture was stirred for 2 hours at room temperature before being evaporated to dryness. The residue was loaded on an IBSIL-C8 5μ 250×20.2 mm column and eluted at 25 ml/min with 30–60% acetonitrile in 5 mM ammonium phosphate gradient over 40 minutes. Fractions containing the desired compound were collected and freeze-dried. The freeze-dried residue was dissolved in water (5 ml) and applied to a Bondesil 40μ C8 resin column, washed with water and eluted with methanol. Evaporation of the methanol gave compound 118 (11.2 mg) as pale yellow solid.

EXAMPLE 2c

Preparation of Compounds 119 and 120

Decyl isocyanate (0.44 g) in dry dimethylformamide (0.2 ml) was added to deacylated Boc-protected daptomycin (3.13 g) in dry dimethylformamide (20 ml). The mixture was stirred at room temperature under nitrogen. After 7 hours the mixture was purified on a Bondesil 40μ C8 resin column with 10% acetonitrile-water followed by 50% acetonitrile-water. The desired fractions were freeze-dried to give compound 119 (1.73 g) as pale yellow solid.

Compound 119 (1.73 g) in dry dichloromethane (20 ml), trifluoroacetic acid (22 ml) and ethane dithiol (0.5 ml) was stirred for 4 hours at room temperature before being evaporated to dryness. The residue was triturated with methanol and diethyl ether then loaded on an IBSIL-C8 $5\mu$ 250×20.2 mm column and eluted at 25 ml/min with 30–60% acetonitrile in 5 mM ammonium phosphate gradient over 40 minutes Fractions containing the desired compound were collected and freeze-dried. The freeze-dried residue was dissolved in water (5 ml) and applied to a Bondesil 40 A C8 resin column, washed with water and eluted with methanol. Evaporation of the methanol gave compound 120 (359.8 mg) as pale yellow solid.

EXAMPLE 3

Preparation of Compounds 3, 5–6, 8–13, 20–24, 34–36, 50, 71 and 75

Daptomycin (250 mg) and N-tBoc-L-tryptophan-p-nitrophenyl ester (144 mg) were stirred in dry dimethylformamide (3 ml) at room temperature for two days. The mixture was loaded on an IBSIL-C8 $5\mu$ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil $40\mu$ C8 resin column, washed with water and eluted with methanol. Evaporation of the methanol gave N-Boc tryptophan daptomycin as a pale yellow solid (130 mg).

A preparation of deacylase enzyme was produced from recombinant *Streptomyces lividans*, which expresses the *Actinoplanes utahensis* deacylase enzyme. The enzyme in ethylene glycol (400 $\mu$l) was added to the solution of N-Boc tryptophan daptomycin (100 mg) in HPLC grade water (20 ml). The solution was adjusted to pH 8.5 with sodium hydroxide (1 M). The mixture was stirred for 24 hours. The mixture was loaded on a C8 resin plug column, washed with water and eluted with methanol. Evaporation of the methanol gave a residue which was applied to an IBSIL-C8 $5\mu$ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil $40\mu$ C8 resin column, washed with water and eluted with methanol. Evaporation of the methanol gave deacylated N-Boc tryptophan daptomycin as a pale yellow solid (42 mg).

Deacylated N-Boc tryptophan daptomycin (20 mg) was stirred in dry dimethylformamide (2 ml) at room temperature. Undecyl isocyanate (2.25 mg) was added to the solution. After stirring at ambient temperature for 24 hours, the mixture was diluted with water (10 ml) and applied to a Bondesil $40\mu$ C8 resin column, washed with water and eluted with methanol, Evaporation of the methanol gave the undecyl urea of N-Boc tryptophan daptomycin as a pale yellow solid (21 mg).

N-Boc tryptophan daptomycin undecyl urea (21 mg) was stirred in trifluoroacetic acid (2 ml) and anisole (0.1 ml) at room temperature for 2 hours. Removal of the solvents under reduced pressure gave a residue which was loaded on an IBSIL-C8 $5\mu$ 250×20.2 mm column and eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil $40\mu$ C8 resin column, washed with water and eluted with methanol. Evaporation of the methanol gave compound 3 as a pale yellow solid (0.8 mg).

In an analogous manner, compounds 5–6, 8–13, 20–24, 34–36, 50, 71 and 75 can be prepared as detailed in the above example by appropriate substitutions of reagents.

EXAMPLE 3a

Preparation of Compound 7

Deacylated N-Boc tryptophan daptomycin (50 mg) and nonaldehyde (4.1 mg) were stirred in dry dimethylformamide (2 ml) at room temperature. Sodium triacetoxy borohydride (3.6 mg) was added to the solution. The mixture was stirred for 24 hours, then loaded on an IBSIL-C8 $5\mu$ 250× 20.2 mm column and eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil $40\mu$ C8 resin column, washed with water and eluted with methanol. Evaporation of the methanol gave nonyl amino N-Boc tryptophan daptomycin as a pale yellow solid (14 mg).

Nonyl amino N-Boc tryptophan daptomycin (14 mg) was stirred in trifluoroacetic acid (2 ml) and anisole (0.1 ml) at room temperature for 2 hours. Removal of the solvents under reduced pressure gave a residue which was loaded on an IBSIL-C8 $5\mu$ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil $40\mu$ C8 resin column, washed with water and eluted with methanol. Evaporation of the methanol gave compound 7 as a pale yellow solid (5 mg)

EXAMPLE 3b

Preparation of Compound 17

Deacylated N-Boc tryptophan daptomycin (50 mg) was stirred in dry dimethylformamide (2 ml) at room temperature. Dodecyl isocyanate (6.0 mg) was added to the solution. The mixture was stirred for 24 hours. The mixture was loaded on an IBSIL-C8 $5\mu$ 250×20.2 mm column and eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil $40\mu$ C8 resin column, washed with water and eluted with methanol. Evaporation of the methanol gave the dodecyl urea of N-Boc tryptophan daptomycin as a pale yellow solid (27 mg).

N-Boc tryptophan daptomycin dodecyl urea (25 mg) was stirred in trifluoroacetic acid (2 ml) and anisole (0.1 ml) at room temperature for 2 hours. Removal of the solvents under reduced pressure gave a residue which was loaded on an IBSIL-C8 $5\mu$ 250×20.2 mm column and eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil $40\mu$ C8 resin column, washed with water and eluted with methanol. Evaporation of the methanol gave compound 17 as a pale yellow solid (4.3 mg).

EXAMPLE 4

Preparation of Compounds 69, 25, 56–58, 62–64, 70, 106 and 108

Daptomycin octyl urea synthesized from deacylated Boc-protected daptomycin by using octyl isocyanate according to examples 1 and 1a (60 mg) and N-tBoc-L-tryptophan-p-nitrophenyl ester (31 mg) were stirred in dry dimethylformamide (2 ml) at room temperature for two days. The mixture was loaded onto an IBSIL-C8 5μ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40μ C8 resin column, washed with water and eluted with methanol. Evaporation of the methanol gave the acylated intermediate as a pale yellow solid (29 mg).

The acylated intermediate (25 mg) was stirred in trifluoroacetic acid (2 ml) and anisole (0.1 ml) at room temperature for 2 hours. Evaporation under reduced pressure gave a residue which was loaded on an IBSIL-C8 5μ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40μ C8 resin column, washed with water and eluted with methanol. Evaporation of the methanol gave compound 69 as a pale yellow solid (5 mg).

In an analogous manner, compounds 25, 56–58, 62–64, 70, 106 and 108 can be prepared by those having skill in the art as detailed in the above example by appropriate substitutions of reagents.

EXAMPLE 4a

Preparation of Compounds 89, 76–78, 87–88 and 113

Daptomycin dodecyl urea synthesized from deacylated Boc-protected daptomycin by using dodecyl isocyanate according to examples 1 and 1a (200 mg) and 2-imidazolecarboxaldehyde (21 mg) in dry dimethylformamide (1.0 ml) was added sodium triacetoxyborohydride (152 mg). The mixture was stirred at room temperature for 24 hours before purification by preparative HPLC. The mixture was loaded on an IBSIL-C8 5μ 250×20.2 mm column and eluted at 25 ml/min with 30–60% acetonitrile in 5 mM ammonium phosphate gradient over 30 minutes. The desired fractions were collected at 21 minutes and freeze-dried. The freeze-dried residue was dissolved in water (3 ml) and applied to a plug of Bondesil 40μ C8 resin (500 mg). The Bondesil resin was washed with water (10 ml) and then the product was eluted with methanol (10 ml). Evaporation of the methanol gave compound 89 as a pale yellow solid (15 mg).

In an analogous manner, compounds 76–78, 87–88 and 113 can be prepared by those having ordinary skill in the art by following the teachings of the disclosure as detailed in the above example by appropriate substitutions of reagents.

EXAMPLE 4b

Preparation of Compound 114

Daptomycin undecyl urea synthesized from deacylated Boc-protected daptomycin using undecyl isocyanate according to examples 1 and 1a (100 mg), and 5-methoxyindole-3-carboxaldehyde (11 mg) in dry dimethylformamide (0.6 ml) was added sodium triacetoxyborohydride (76 mg). The mixture was stirred at room temperature for 24 hours before purification by preparative HPLC. The mixture was loaded on an IBSIL-C8 5μ 250×20.2 mm column and eluted at 25 ml/min with 30–60% acetonitrile in 5 mM ammonium phosphate gradient over 30 minutes. The desired fractions were collected at 21 minutes and freeze-dried. The freeze-dried residue was dissolved in water (2 ml) and applied to a plug of Bondesil 40μ C8 resin (500 mg). The Bondesil resin was washed with water (10 ml) and then the product was eluted with methanol (10 ml). Evaporation of the methanol gave compound 114 as a pale yellow solid (10 mg).

EXAMPLE 5

Compounds according to Formula I were tested for antimicrobial activity against a panel of organisms according to standard procedures described by the National Committee for Clinical Laboratory Standards (NCCLS document M7-A5, Vol. 20, No. 2, 2000) except that all testing was performed at 37° C. Compounds were dissolved in 100% dimethyl sulfoxide and were diluted to the final reaction concentration (0.1 μg/mL–100 μg/mL) in microbial growth media. In all cases the final concentration of dimethyl sulfoxide incubated with cells is less than or equal to 1%. For minimum inhibitory concentration (MIC) calculations, 2-fold dilutions of compounds were added to wells of a microtiter plate containing $5 \times 10^4$ bacteria cells in a final volume of 100 μL of media (Mueller-Hinton Broth supplemented with 50 mg/L $Ca^{2+}$). The optical densities (OD) of the bacterial cells, which measures bacterial cell growth and proliferation, were measured using a commercial plate reader. The MIC value is defined as the lowest compound concentration inhibiting growth of the test organism. The MIC (in μg/ml) values of representative compounds of the present invention are listed in Table VI.

EXAMPLE 6

The in vivo antibacterial activity of Compound 2 (see Table IV) was established by infecting female CD-1 mice (Charles River Lab, Mass. ) weighing 19–23 g intraperitoneally with Methicillin Resistant S. aureus (MRSA) inoculum. The inoculum was prepared from Methicillin Resistant S. aureus (ATCC 43300). The MRSA inoculum was cultured in Mueller-Hinton (MH) broth at 37° C. for 18 hours. The optical density at 600 nm ($OD_{600}$) was determined for a 1:10 dilution of the overnight culture. Bacteria ($8 \times 10^8$ cfu) was added to 20 ml of phosphate buffered saline (Sigma P-0261) containing 6% hog gastric mucin (Sigma M-2378). Group 1–5 animals were injected with 0.5 ml of the inoculum, equivalent to $2 \times 10^7$ cfu/mouse, which is the dose causing ~100% death of the animals without treatment. Group 6 animals received no inoculum.

The test compound (10 mg) was dissolved in 10.0 ml of 50 mM phosphate buffer to give a solution of 1 mg/ml (pH=7.0). This solution was serially diluted with vehicle by 4-fold (1.5 ml to 6 ml) to give 0.25, 0.063 and 0.016 mg/ml solutions. All the solutions were filtered with 0.2 μm Nalgene syringe filter. Immediately after the bacterial inoculation, group 1 animals were subcutaneously (sc) injected with buffer (no test compound) and groups 2 to 5 were given test compound sc at 10, 2.5, 0.63, and 0.16 mg/kg, respectively. Group 6 animals compound 2 s.c at 10 mg/kg only. These injections were repeated once at 4 hours after the inoculation for the respective groups. The injection volume at each time was 10 ml per kilogram of body weight.

The results of the in vivo efficacy test are summarized in Table IV, which provides a representative example of the results obtained for Compound 2. The 50% effective dose ($ED_{50}$) is calculated on the basis of the number of mice surviving 7 days after inoculation. The $ED_{50}$ in mg/kg of other representative compounds of the present invention are listed in Table V.

TABLE V

| Group | # of mice | Inoculated with | Treatment | Survival (7 days) |
|---|---|---|---|---|
| 1 | 5 | MRSA #43300 2 × 10$^7$ cfu/mouse | Phosphate buffer 10 ml/kg, s.c. x2 | 0/5 |
| 2 | 5 | MRSA #43300 2 × 10$^7$ cfu/mouse | Compound 2 10 mg/kg, s.c. x2 | 5/5 |
| 3 | 5 | MRSA #43300 2 × 10$^7$ cfu/mouse | Compound 2 2.5 mg/kg, s.c. x2 | 5/5 |
| 4 | 5 | MRSA #43300 2 × 10$^7$ cfu/mouse | Compound 2 0.63 mg/kg, s.c. x2 | 5/5 |
| 5 | 5 | MRSA #43300 2 × 10$^7$ cfu/mouse | Compound 2 0.16 mg/kg, s.c. x2 | 1/5 |
| 6 | 5 | NO | Compound 2 10 mg/kg s.c. x2 | 5/5 |

The $ED_{50}$ of compound 2 is calculated to be 0.43 mg/kg.
The $ED_{50}$ was determined for other compounds of this invention in a similar manner.

TABLE VI

| Compound # | MIC (μg/ml) S. aureus | MIC (μg/ml) E. faecalis | $ED_{50}$ (mg/kg) |
|---|---|---|---|
| 1 | ++ | + | |
| 2 | +++ | ++ | +++ |
| 3 | +++ | +++ | +++ |
| 5 | ++ | ++ | |
| 6 | + | | |
| 7 | + | + | |
| 8 | ++ | + | |
| 9 | ++ | + | |
| 10 | ++ | + | |
| 11 | + | + | |
| 12 | + | + | |
| 13 | ++ | + | |
| 17 | +++ | +++ | |
| 18 | +++ | ++ | +++ |
| 19 | | | |
| 20 | + | | |
| 21 | + | | |
| 22 | + | | |
| 23 | ++ | | |
| 24 | +++ | + | |
| 25 | ++ | + | |
| 34 | +++ | ++ | |
| 35 | ++ | + | |
| 36 | + | | |
| 37 | ++ | + | |
| 38 | +++ | ++ | |
| 39 | +++ | +++ | |
| 40 | + | | |
| 41 | | | |
| 43 | | | |
| 44 | ++ | + | |
| 45 | +++ | ++ | |
| 46 | ++ | + | |
| 47 | +++ | +++ | |
| 48 | +++ | +++ | +++ |
| 49 | ++ | ++ | |
| 50 | +++ | ++ | |
| 56 | ++ | + | |
| 57 | ++ | ++ | |
| 58 | ++ | ++ | |
| 62 | ++ | + | |
| 63 | +++ | ++ | |
| 64 | +++ | ++ | |
| 69 | +++ | + | |
| 70 | | | |
| 71 | +++ | + | |
| 72 | +++ | + | |
| 73 | +++ | ++ | |
| 74 | +++ | ++ | |
| 75 | +++ | ++ | |
| 76 | ++ | + | |
| 77 | +++ | + | |
| 78 | ++ | + | |
| 87 | +++ | ++ | |
| 88 | +++ | ++ | |
| 89 | +++ | +++ | |
| 100 | + | | |
| 106 | ++ | + | |
| 108 | | ++ | |
| 109 | ++ | + | |
| 110 | +++ | ++ | |
| 111 | +++ | ++ | |
| 112 | +++ | +++ | |
| 113 | ++ | ++ | |
| 114 | +++ | +++ | |
| 115 | ++ | + | |
| 116 | +++ | ++ | |
| 117 | ++ | + | |
| 118 | +++ | +++ | |
| 119 | +++ | ++ | |
| 120 | +++ | +++ | |
| 123 | ++ | | |
| 124 | ++ | +++ | |
| 125 | ++ | +++ | |

Wherein "+++" indicates that the compound has an MIC (μg/ml) of 1 μg/ml or less or an $ED_{50}$ of 1 mg/kg or less;

"++" indicates that the compound has an NEC (μg/ml) or an $ED_{50}$ (mg/kg) or more than 1 μg/ml or 1 mg/kg, respectively, but less than or equal to 10 μg/ml or 10 mg/kg, respectively;

"+" that the compound has an MIC (μg/ml) of greater than 10 μg/ml or an $ED_{50}$ of greater than 10 mg/kg; and wherein a blank indicates that the MIC or $ED_{50}$ was not determined.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those or ordinary skill in the art in light of the teachings of this invention that certain changes and modifications may be made thereto without departing from the spirit or scope of the appended claims.

We claim:
1. A compound having the formula (I):

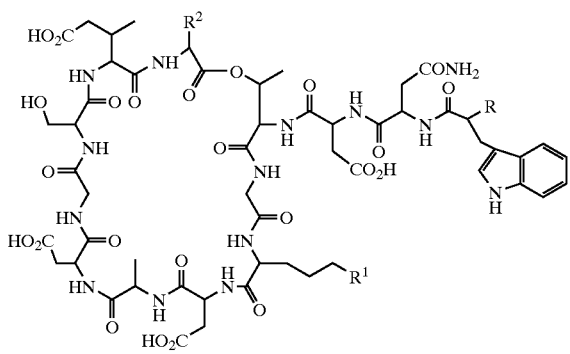

(I)

and salts thereof; wherein R is:

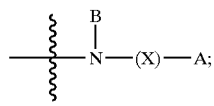

wherein X and X" are independently selected from C=O, C=S, C=NH, C=NR$^X$, S=O or SO$_2$;
wherein R$^X$ is selected from alkyl, alkenyl, alkynyl, aryl, heteroaryl, cycloalkyl, heterocyclyl, hydroxyl, alkoxy, carboxy or carboalkoxy;
wherein B is X"R$^Y$, H, alkyl, alkenyl, alkynyl, aryl, heteroaryl, cycloalkyl and heterocyclyl; and
wherein R$^Y$ is selected from hydrido, alkyl, alkenyl, alkynyl, aryl, heteroaryl, cycloalkyl, heterocyclyl or hydroxyl;
wherein A is H, NH$_2$, NHR$^A$, NR$^A$R$^B$, heteroaryl, cycloalkyl or heterocyclyl;
wherein R$^A$ and R$^B$ are independently selected from alkyl, alkenyl, alkynyl, aryl, heteroaryl, cycloalkyl, heterocyclyl or carboalkoxy;
provided that when B is H and X is C=O, then A is other than
(a) a pyridinyl ring substituted with a single NHC(O)R$^D$ substitutent or
(b) a (C$_5$–C$_6$) saturated cycloalkyl ring substituted with a single NHC(O)R$^D$ substitutent, wherein R$^D$ is (C$_2$–C$_{17}$) unsubstituted alkyl or (C$_2$–C$_{17}$) unsubstituted alkenyl;

wherein R$^1$ is

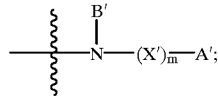

wherein X' and X" are independently selected from C=O, C=S, C=NH, C=NR$^{X'}$, S=O or SO$_2$;
wherein m is 0 or 1;
wherein R$^{X'}$ is selected from alkyl, alkenyl, alkynyl, aryl, heteroaryl, cycloalkyl, heterocyclyl, hydroxyl, alkoxy, carboxy or carboalkoxy;
wherein B' is X'''R$^{Y'}$, H, alkyl, alkenyl, alkynyl, aryl, heteroaryl, cycloalkyl or heterocyclyl;
wherein R$^{Y'}$ is selected from hydrido, alkyl, alkenyl, alkylnyl, aryl, heteroaryl, cycloalkyl, heterocyclyl or hydroxyl;
wherein A' is H, NH$_2$, NHR$^{A'}$, NR$^{A'}$R$^{B'}$, alkyl, alkenyl, alkynyl, alkoxy, aryloxy, aryl, heteroaryl, cycloalkyl or heterocyclyl;
wherein R$^{A'}$ and R$^{B'}$ are independently selected from alkyl, alkenyl, alkynyl, aryl, heteroaryl, cycloalkyl, heterocyclyl or carboalkoxy;
wherein when m is 0, then A' is additionally selected from the group consisting of:

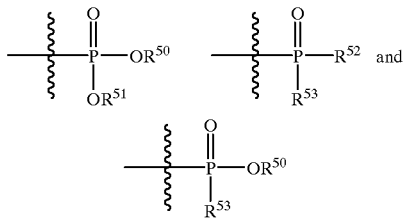

wherein each of R$^{50}$—R$^{53}$ is independently selected from C$_1$–C$_{15}$ is alkyl;
alternatively, wherein B' and A' together form a 5–7 membered heterocyclic or heteroaryl ring;

69 wherein $R^2$ is wherein K and K' together form a $C_3$–$C_7$ cycloalkyl or heterocyclyl ring or a $C_5$–$C_{10}$ aryl or heteroaryl ring;

wherein J is selected from the group consisting of hydrido, amino, $NHR^J$, $NR^JR^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo, wherein each of $R^{24}$, $R^{25}$, and $R^{26}$ is independently selected from the group consisting of alkyl, cycloalkyl, heterocyclyl, aryl and heteroaryl; or $R^{24}$ and $R^{25}$ together form a 5–8 membered heterocyclyl ring;

wherein $R^J$ and $R^K$ are independently selected from alkyl, alkenyl, alkynyl, aryl, heteroaryl, cycloalkyl or heterocyclyl; or alternatively, wherein J, together with $R^{17}$, forms a 5–8 membered heterocyclyl or cycloalkyl ring; or alternatively, wherein J, together with both $R^{17}$ and $R^{18}$, forms a 5–8 membered aryl, cycloalkyl, heterocyclyl or heteroaryl ring; and wherein each of $R^{17}$ and $R^{18}$ is independently selected from the group consisting of hydrido, halo, hydroxyl, alkoxy, amino, thio, sulfinyl, sulfonyl and or wherein $R^{17}$ and $R^{18}$ taken together can form a group consisting of ketal, thioketal, wherein each of $R^{22}$ and $R^{23}$ is independently selected from the group consisting of hydrido and alkyl.

70

2. A compound having the formula (I):

and salts thereof; wherein R is:

wherein X and X" are independently selected from C=O, C=S, C=NH, C=$NR^X$, S=O or $SO_2$;

wherein $R^X$ is selected from alkyl, alkenyl, alkynyl, aryl, heteroaryl, cycloalkyl, heterocyclyl, hydroxyl, alkoxy, carboxy or carboalkoxy;

wherein B is X"$R^Y$, H, alkyl, alkenyl, alkynyl, aryl, heteroaryl, cycloalkyl or heterocyclyl; and wherein $R^Y$ is selected from hydrido, alkyl, alkenyl, alkynyl, aryl, heteroaryl, cycloalkyl, heterocyclyl or hydroxyl;

wherein A is aryl;

provided that when B is H and X is C=O, then A is other than a phenyl ring substituted with either:

(a) —O—(($C_8$–$C_{15}$) unsubstituted alkyl), wherein said phenyl ring may be further optionally substituted with one substituent selected from halo, nitro, ($C_1$–$C_3$) alkyl, hydroxyl, ($C_1$–$C_3$) alkoxy or ($C_1$–$C_3$) alkylthio; or (b) —NHC(O)$R^D$, wherein the phenyl ring maybe further optionally substituted with 1–2 substituents independently selected from amino, nitro, ($C_1$–$C_3$) alkyl, hydroxyl, ($C_1$–$C_3$) alkoxy, halo, mercapto, ($C_1$–$C_3$) alkylthio, carbamyl or ($C_1$–$C_3$) alkylcarbamyl, wherein $R^D$ is ($C_1$–$C_{17}$) unsubstituted alkyl or ($C_2$–$C_{17}$) unsubstituted alkenyl;

wherein $R^1$ is wherein X' and X'" are independently selected from C=O, C=S, C=NH, C=$NR^{X'}$, S=O or $SO_2$;

wherein m is 0 or 1;

wherein $R^{X'}$ is selected from alkyl, alkenyl, alkynyl, aryl, heteroaryl, cycloalkyl, heterocyclyl, hydroxyl, alkoxy, carboxy or carboalkoxy;

wherein B' is X'"$R^{Y'}$, H, alkyl, alkenyl, alkynyl, aryl, heteroaryl, cycloalkyl or heterocyclyl;

wherein $R^{Y'}$ selected from hydride, alkyl, alkenyl, alkynyl, aryl, heteroaryl, cycloalkyl, heterocyclyl or hydroxyl;

wherein A' is H, NH₂, NHR$^{A'}$, NR$^{A'}$R$^{B'}$, alkyl, alkenyl, alkynyl, alkoxy, aryloxy, aryl, heteroaryl, cycloalkyl or heterocyclyl;

wherein R$^{A'}$ and R$^{B'}$ are independently selected from alkyl, alkenyl, alkynyl, aryl, heteroaryl, cycloalkyl, heterocyclyl or carboalkoxy;

wherein when m is 0, then A' is additionally selected from the group consisting of:

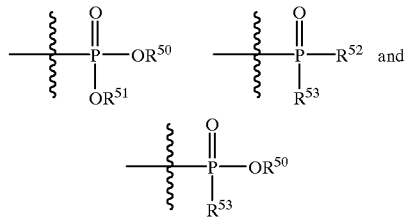

wherein each of R$^{50}$–R$^{53}$ is independently selected from C₁–C₁₅ alkyl;

alternatively, wherein B' and A' together form a 5–7 membered heterocyclic or heteroaryl ring;

wherein R² is

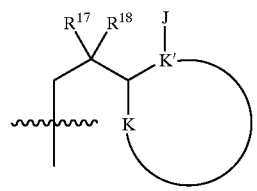

wherein K and K' together form a C₃–C₇ cycloalkyl or heterocyclyl ring or a C₅–C₁₀ aryl or heteroaryl ring;

wherein J is selected from the group consisting of hydrido, ammo, NHR$^J$, NR$^J$R$^K$, alkyl, alkenyl, alkynyl, alkoxy, aryloxy, aryl, heterocyclyl, cycloalkyl, heterocyclyl, alkylamino, hydroxyl, thin, alkylthio, alkenylthio, sulfinyl, sulfonyl, azido, cyano, halo,

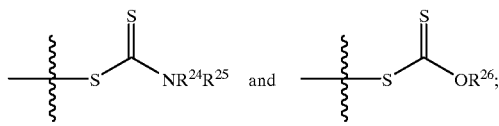

wherein each of R$^{24}$, R$^{25}$, and R$^{26}$ is independently selected from the group consisting of alkyl, cycloalkyl, heterocyclyl, aryl and heteroaryl; or R$^{24}$ and R$^{25}$ together form a 5–8 membered heterocyclyl ring;

wherein R$^J$ and R$^K$ are independently selected from alkyl, alkenyl, alkynyl, aryl, heteroaryl, cycloalkyl or heterocyclyl; or alternatively, wherein J, together with R$^{17}$, forms a 5–8 membered heterocyclyl or cycloalkyl ring; or alternatively, wherein J, together with both R$^{17}$, together with both R$^{17}$ and R$^{18}$, forms a 5–8 membered aryl, cycloalkyl, heterocyclyl or heteroaryl ring; and wherein each of R$^{17}$ and R$^{18}$ is independently selected from the group consisting of hydrido, halo, hydroxyl, alkoxy, amino, thio, sulfinyl, sulfonyl and

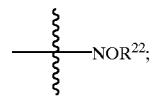

or wherein R$^{17}$ and R$^{18}$ taken together can form a group consisting of ketal, thioketal,

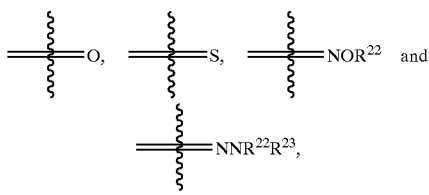

wherein each of R$^{22}$ and R$^{23}$ is independently selected from the group consisting of hydrido and alkyl.

3. The compound according to claim 1, wherein R is selected from the group consisting of:

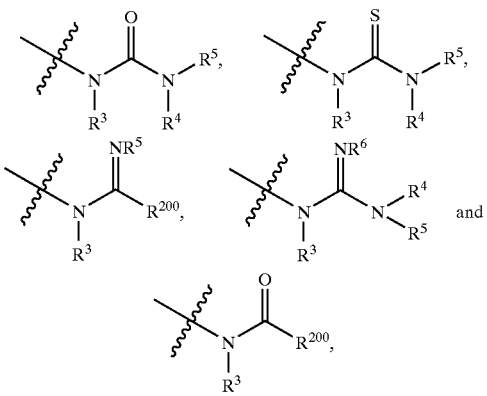

wherein each of R³, R⁴, R⁵, and R⁶ is independently selected from the group consisting of hydrido, alkyl, aryl, heterocyclyl and heteroaryl, and wherein R$^{200}$ is selected from the group consisting of hydrido, heterocyclyl, and heteroaryl.

4. The compound according to claim 3, wherein R is selected from

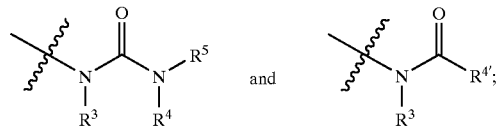

and wherein R$^{4'}$ is selected from the group consisting of heteroaryl, and heterocyclyl.

5. The compound according to claim 4, wherein R is

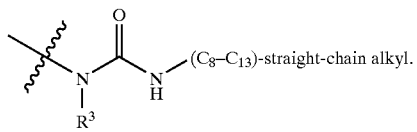

6. The compound according to either of claim 1 or 2, wherein R¹ is selected from the group consisting of:

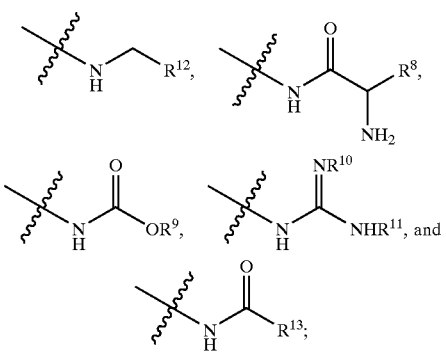

wherein R[8] is selected from a natural amino acid side chain or an amino acid side chain;

wherein each of R[9], R[10] and R[11] is selected from the group consisting of hydrido, alkyl, aryl, heterocyclyl and heteroaryl;

wherein R[12] is selected from the group consisting of heterocyclyl, heteroaryl, aryl, and alkyl and wherein R[13] is selected from (C$_1$–C$_3$-alkyl) and aryl.

7. The compound according to claim 6, wherein R[1] is selected from the group consisting of:

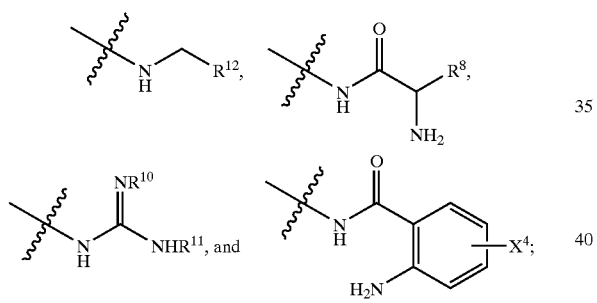

wherein R[8] is selected from tryptophan side chain and lysine side chain;

wherein each of R[10] and R[11] is independently selected from hydrido and alkyl;

wherein R[12] is selected from imidazolyl, N-methylimidazolyl, indolyl, quinolinyl, benzyloxybenzyl, and benzylpiperidenylbenzyl; and wherein X[4] is fluoro, or trifluoromethyl.

8. The compound according to either of claim 1 or 2, wherein J is selected from the group consisting of hydrido, amino, azido and

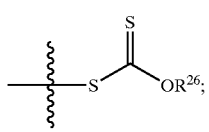

wherein R[17] and R[18] taken together form a group selected from ketal,

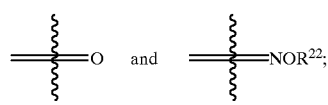

or wherein R[17] is hydroxyl when R[18] is hydrido;
or wherein J, together with R[17], forms a heterocyclyl ring.

9. The compound according to claim 8, wherein R[2] is selected from the group consisting of

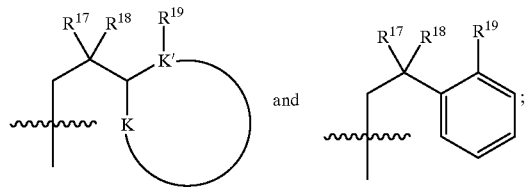

wherein R[17] and R[18] taken together form a group selected from

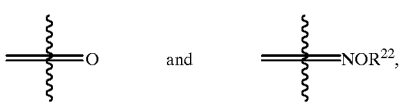

wherein R[22] is selected from the group consisting of H and alkyl; and wherein R[19] is selected from the group consisting of hydrido, amino, azido and

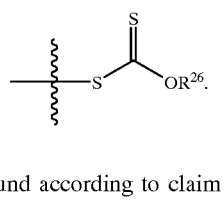

10. The compound according to claim 9, wherein R[2] is

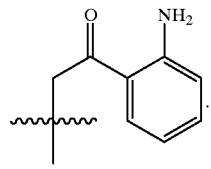

11. A pharmaceutical composition comprising the compound according to either of claim 1 or 2 and a pharmaceutically acceptable carrier.

12. A method of treating a bacterial infection in a subject, comprising the step of administering a therapeutically-effective amount of the pharmaceutical composition according to claim 11 to a subject in need thereof for a time and under conditions effective to ameliorate said bacterial infection.

13. The method according to claim 12, wherein said subject is selected from the group consisting of a human, an animal, a cell culture and a plant.

14. The method according to claim 12, wherein said bacterial infection is caused by a gram-positive bacteria.

15. The method according to claim 14, wherein said bacteria is an antibiotic-resistant bacteria that is resistant to an antibiotic that is not included within the scope of Formula (I).

16. The method according to claim 15, wherein said antibiotic-resistant bacteria are resistant to an antibiotic selected from the group consisting of vancomycin, methicillin, glycopeptide antibiotics, penicillin and daptomycin.

17. The method according to claim 12, further comprising the step of co-administering more than one compound of Formula (I) according to either of claim 1 or 2 to a subject in need thereof.

18. The method according to claim 12, further comprising the step of co-administering a second antimicrobial agent wherein said second antimicrobial agent is not included within the scope of Formula (I).

19. The method according to claim 11, wherein said second antimicrobial agent is selected from the group consisting of penicillins, carbapenems, cephalosporins, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents, trimethoprim, pyrimethamine, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomicin, glycopeptide, glycylcycline, ketolides, oxazolidinone, imipenem, amikacin, netilmicin, fosfomycin, gentamicin, ceftriaxone, ZIRACIN, (56-deacetyl-57-demethyl-45-O-de(2-methyl-1-oxopropyl)-12-O-(2,3,6-trideoxy-3-C-methyl-4-O-methyl-3-nitro-alpha-L-arabino-hexopyranosyl)flambamycin), LY333328 (oritavancin), linezolid (N-[[((5S)-3-[3-fluoro-4-(4-morpholinyl)phenyl]-2-oxo-5-oxazolidinyl]methyl]acetatamide), SYNERCID (dalfopristin-quinupristin), aztreonam (2-[[(Z)-[1-(2-amino-4-thiazolyl)-2-[[(2S,3S)-2-methyl-4-oxo-1-sulfo-3-azetidinyl]amino]-2-oxoethylidene]amino]oxy]-2-methyl-propanoic acid), metronidazole(2-methyl-5-nitro-1H-imidazole-1-ethanol), epiroprim (5-[[3,5-diethoxy-4-(1H-pyrrol-1-yl)phenyl]methyl]-2,4-pyrimidinediamine), OCA-983 (1-[[(2S)-2-amino-3-methyl-1-oxobutyl]amino]-2,5-anhydro-3-S-[(4R,5S,6S)-2-carboxy-6-[(1R)-1-hydxoxyethyl]-4-methyl-7-oxo-1-azabicyclo[3.2.0]hept-2-en-3-yl]-1,4-dideoxy-3-thio-D-threo-pentitol), GV-143253 (trinem), sanfetrinem ((1S, 5S, 8aS, 8bR)-1,2, 5, 6, 7, 8, 8a, 8b-octahydro-1-[(1R)-1-hydroxyethyl]-5-methoxy-2-oxo-azeto[2,1-a]isoindole-4-carboxylic acid), CS-834 ((4R, 5S, 6S)-6-[(IR)-1-hydroxyethyl]-4-methyl-7-oxo-3-[[((3R)-5-oxo-3-pyrrolidinyl]thio]-1-azabicyclo[3.2.0]hept-2-ene-2-carboxylic acid (2,2-dimethyl-1-oxopropoxy)methyl ester), biapenem (6-[[(4R,5S,6S)-2-carboxy-6-[(1R)-1-hydroxyethyl]-4-methyl-7-oxo-1-azabicyclo[3.2.0]hept-2-en-3-yl]thio]-6,7-dihydro-5H-pyrazolo[1,2-a][1,2,4]triazol-4-ium inner salt), KA 159 (stipiamide), dynemicin A ((1S, 4R,4aR,14S,14aS,18Z)-1,4,7,12,13,14-hexahydro-6,8,11-trihydroxy-3-methoxy-1-methyl-7,12-dioxo-4a,14a-epoxy-4,14-[3]hexene[1,5]diynonaphtho[2,3-c]phenanthridine-2-carboxylic acid), DX8739 ((4R,5S,6S)-3-[[(3S,5S)-5-[[4-[(2S)-5-amino-2-hydroxy-1-oxopentyl]-1-piperazinyl]carbonyl]-3-pyrrolidinyl]thio]-6-[(1R)-1-hydroxyethyl]-4-methyl-7-oxo-1-azabicyclo[3.2.0]hept-2-ene-2-carboxylic acid), DU 6681 ((4R,5S,6S)-3-[[(6S)-6,7-dihydro-5H-pyrrolo[1,2-a]imidazol-6-yl]thio]-6-[(1R)-1-hydroxyethyl]-4-methyl-7-oxo-1-azabicyclo[3.2.0]hept-2-ene-2-carboxylic acid), cefluprenam ((2E)-N-(2-amino-2-oxoethyl)-3-[(6R,7R)-7-[[(2Z)-(5-amino-1,2,4-thiadiazol-3-yl)[(fluoro methoxy)imino]acetyl]amino]-2-carboxy-8-oxo-5-thia-1-azabicyclo[4.2.0]oct-2-en-3-yl]-N-ethyl-N-methyl-2-propen-1-aminium inner salt), ER 35786 ((4R,5S,6S)-6-[(1R)-1-hydroxyethyl]-3-[[(3S,5S)-5-[(R)-hydroxy(3R)-3-pyrrolidinylmethyl]-3-pyrrolidinyl]thio]-4-methyl-7-oxo-1-azabicyclo[3.2.0]hept-2-ene-2-carboxylic acid monohydrochloride), cefoselis ((6R,7R)-7-[[(2Z)-(2-amino-4-thiazolyl)(methoxy imino)acetyl]amino]-3-[[2,3-dihydro-2-(2-hydroxyethyl)-3-imino-1H-pyrazol-1-yl]methyl]-8-oxo-5-thia-1-azabicyclo[4.2.0]oct-2-ene-2-carboxylic acid), sanfetrinem celexetil ((1S,5S,8aS,8bR)-1,2,5,6,7,8,8a,8b-octahydro-1-[(1R)-1-hydroxyethyl]-5-methoxy-2-oxo-azeto[2,1-a]isoindole-4-carboxylic acid 1-[(cyclohexyloxy)carbonyl]oxy]ethyl ester), cefpirome (1-[[[(6R,7R)-7-[[(2Z)-(2-amino-4-thiazolyl)(methoxyimino)acetyl]amino]-2-carboxy-8-oxo-5-thia-1-azabicyclo[4.2.0]oct-2-en-3-yl]methyl]-6,7-dihydro-5H-cyclopenta[b]pyridinium inner salt), HMR-3647 (3-de[(2,6-dideoxy-3-C-methyl-3-O-methyl-alpha-L-ribo-hexopyranosyl)oxy]-11,12-dideoxy-6-O-methyl-3-oxo-12,11-[oxycarbonyl[[4-(4-(3-pyridinyl)-1H-imidazol-1-yl]butyl]imino]]-erythromycin), RU-59863 (C-7 catechol substituted cephalosporin), KP 736 ((6R,7R)-7-[[(2Z)-(2-amino-4-thiazolyl)[[(1,4-dihydro-1,5-dihydroxy-4-oxo-2-pyridinyl)methoxy]imino]acetyl]amino]-8-oxo-3-[(1,2,3-thiadiazol-5-ylthio)methyl]-5-thia-1-azabicyclo[4.2.0]oct-2-ene-2-carboxylic acid disodium salt), Rifalazil (1',4-didehydro-1-deoxy-1,4-dihydro-3'-hydroxy-5'-[4-(2-methylpropyl)-1-piperazinyl]-1-oxo-rifamycin VIII), MEN 10700 ((5R,6S)-3-[[(2-amino-2-oxoethyl)methylamino]methyl]-6-[(1R)-1-hydroxyethyl]-7-oxo-4-thia-1-azabicyclo[3.2.0]hept-2-ene-2-carboxylic acid), lenapenem ((4R,5S,6S)-6-[(1R)-1-hydroxyethyl]-3-[[(3S,5S)-5-[(1R)-1-hydroxy-3-(methylamino)propyl]-3-pyrrolidinyl]thio]-4-methyl-7-oxo-1-azabicyclo[3.2.0]hept-2-ene-2-carboxylic acid), BO 2502A ((4R,5S,6S)-3-[(2S, 3'S,4S)-[2,3'-bipyrrolidin]-4-ylthio]-6-[(1R)-1-hydroxyethyl]-4-methyl-7-oxo-1-azabicyclo[3.2.0]hept-2-ene-2-carboxylic acid), NE-1530 (3'-sialyllacto-N-neotetraose), PR 39 (L-arginyl-L-arginyl-L-arginyl-L-prolyl-L-arginyl-L-prolyl-L-prolyl-L-tryosyl-L-leucyl-L-prolyl-L-arginyl-L-prolyl-L-arginyl-L-prolyl-L-prolyl-L-prolyl-L-phenylalanyl-L-phenylalanyl-L-prolyl-L-prolyl-L-arginyl-L-leucyl-L-prolyl-L-prolyl-L-arginyl-L-isoleucyl-L-prolyl-L-prolylglycyl-L-phenylalanyl-L-prolyl-L-prolyl-L-arginyl-L-phenylalanyl-L-prolyl-L-prolyl-L-arginyl-L-phenylalanyl-L-prolinamide [SEQ ID NO: 1[), K130 (5-[[4-[3-[[4-[(4-aminophenyl)sulfonyl]phenyl]amino]propoxy]-3,5-dimethoxyphenyl]methyl]-2,4-pyrimidinediamine), PD 138312 ((R)-7-[3-(1-amino-1-methylethyl)-1-pyrrolidinyl]-1-cyclopropyl-6-fluoro-1,4-dihydro-4-oxo-1,8-naphthyridine-3-carboxylic acid), PD 140248 (7-[(3R)-3-[(1S)-1-aminoethyl]-1-pyrrolidinyl]-1-(2,4-difluorophenyl)-6-fluoro-1,4-dihydro-4-oxo-1,8-naphthyridine-3-carboxylic acid), CP 111905 (5-deoxy-5-[[(2E)-3-[3-hydroxy-4-(2-propenyloxy)phenyl]-2-methyl-1-oxo-2-propenyl]amino]-1,2-O-mehyle-D-neo-inositol), sulopenem ((5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylic acid), ritipenam acoxyl ((5R,6R)-3-[[(aminocarbonyl)oxy]methyl]-6-[(1R)-1-hydroxyethyl]-7-oxo-4-thia-1-azabicyclo[3.2.0]hept-2-ene-2-carboxylic acid (acetyloxy)methyl ester), RO-65-

5788 ((6R,7R)-7-[[(2Z)-(5-amino-1,2,4-thiadiazol-3-yl)(hydroxyimino)acetyl]amino]-3-[(E)-[(3'R)-1'-[[(5-methyl-2-oxo-1,3-dioxol-4-yl)methoxy]carbonyl]-2-oxo[1,3'-bipyrrolidin]-3-ylidene]methyl]-8-oxo-5-thia-1-azabicyclo[4.2.0]oct-2-ene-2-carboxylic acid monosodium salt), Sch-40832 (N-[[48-[1-[[2,6-dideoxy-3-O-(2,6-dideoxy-D-arabino-hexopyranosyl)-D-arabino-hexopyranosyl]oxy]ethyl]-15-ethylidene-1,3a,4,5,10,11,12,13,14,15,19,20,21,22,28,29,41,42-octadecahydro-41-hydroxy-12,45-bis(1-hydroxyethyl)-1-(hydroxymethyl)-22-(1-hydroxy-1-methylpropyl)-36-methyl-51,54,57-tris(methylene)-3-(methylthio)-10,13,20,27,38,49,52,55,58-nanaoxo-18H,27H-5a,29-(iminoethaniminoethanimino ethaniminoethanimino[7,2]quinolinomethanoxy methano)-9,6:19,16:26,23:33,30-tetranitrilo-16H,33aH-imidazo[1',5':1,6]pyrido [3,2-m][1,11,17,24,4,7,20,27]tetrathiatetraazacyclotriacontin-1-yl]carbonyl]-2,3-didehydroalanyl-2,3-didehydro-alanine methyl ester stereoisomer), micacocidin A ((OC-6-26-A)-[(4S)-2-[(2S)-2-[(2R,4R)-2-[(4R)-4,5-dihydro-2-[2-(hydroxy-.kappa.O)-6-pentylphenyl]-4-thiazolyl-.kappa.N3]-3-methyl-4-thiazolidinyl-.kappa.N3]-2-(hydroxy-.kappa.O)-1,1-dimethylethyl]-4,5-dihydro-4-methyl-4-thiazolecarboxylato(2-)-.kappa.N3, .kappa.O4]-Zinc), SR-15402 ((1S,5S,8aS,8bR)-1,2,5,6,7,8,8a,8b-octahydro-1-[(1R)-1-hydroxyethyl]-2-oxo-5-[(3S)-3-pyrrolidinylthio]-azeto[2,1-a]isoindole-4-carboxylic acid TOC 39 (1-(2-amino-2-oxoethyl)-4-[[(1E)-2-[(6R,7R)-7-[[(2Z)-(2-amino-4-thiazolyl) (hydroxyimino)acetyl]amino]-2-carboxy-8-oxo-5-thia-1-azabicyclo[4.2.0]oct-2-en-3-yl]ethenyl]thio]-pyridinium inner salt), carumonam ([[(Z)-[2-[[(2S,3S)-2-[[(aminocarbonyl)oxy]methyl]-4-oxo-1-sulfo-3-azetidinyl]amino]-1-(2-amino-4-thiazolyl)-2-oxoethylidene]amino]oxy]-acetic acid), cefozopran (1-[[[(6R,7R)-7-[[(2Z)-5-amino-1,2,4-thiadiazol-3-yl)(methoxy imino)acetyl]amino]-2-carboxy-8-oxo-5-thia-1-azabicyclo[4.2.0]oct-2-en-3-yl]methyl]-imidazo[1,2-b]pyridazinium inner salt), cefetamet pivoxil ((6R,7R)-7-[[(2Z)-(2-amino-4-thiazolyl)(methoxy imino)acetyl]amino]-3-methyl-8-oxo-5-thia-1-azabicyclo[4.2.0]oct-2-ene-2-carboxylic acid (2,2-dimethyl-1-oxopropoxy)methyl ester), and T 3811 (des-F(6)-quinolone).

20. The method according to claim 18, wherein said antimicrobial agent is selected from the group consisting of imipenen, amikacin, netilmicin, fosfomycin, gentamicin, celhiaxone, teicoplanin, ZIRACIN (56-deacetyl-57-demethyl-45-O-de(2-methyl-1-oxopropyl)-12-O-(2,3,6-trideoxy-3–C-methyl-4-O-methyl-3-nitro-alpha-L-arabino-hexopyranosyl)flambamycin), LY333328 (oritavancin), HMR-3647 (3-de[(2,6-dideoxy-3–C-methyl-3-O-methyl-alpha-L-ribo-hexopyranosyl)oxy]-11,12-dideoxy-6-O-methyl-3-oxo-12,11-[oxycarbonyl[[4-[4-(3-pyridinyl)-1H-imidazol-1-yl-]butyl]imino]]-erythromycin), linezolid (N-[[(5S)-3-[3fluoro-4-(4-morpholinyl)phenyl]-2-oxo-5-oxazolidinyl]methyl]acetamide), SYNERCID (dalfopristin-quinupristin), aztreonam (2-[[(Z)-[1-(2-amino-4-thiazolyl)-2-[[(2S,3S)-2-methyl-4-oxo-1sulfo-3-azetidinyl]amino]-2-oxoethylidene]amino]oxy-2-methyl-propanoic acid), and metronidazole (2-methyl-5-nitro-1H-imidazole-1-ethanol).

21. The method according to claim 13, wherein said subject is selected from the group consisting of a human and an animal.

22. The method according to claim 21, wherein said subject is a human.

23. The compound of claim 1 having the formula (II):

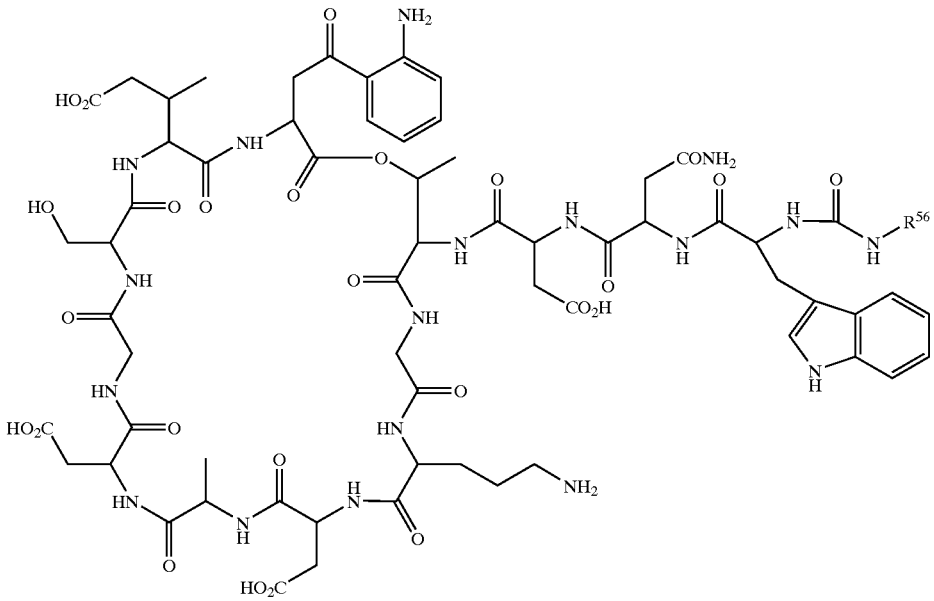

(II)

wherein $R^{56}$ is an optionally substituted straight-chain $C_8$–$C_{14}$ alkyl group.

24. A method of using the compound according to claim 23 to make a compound according to either of claim 1 or 2 of the formula:

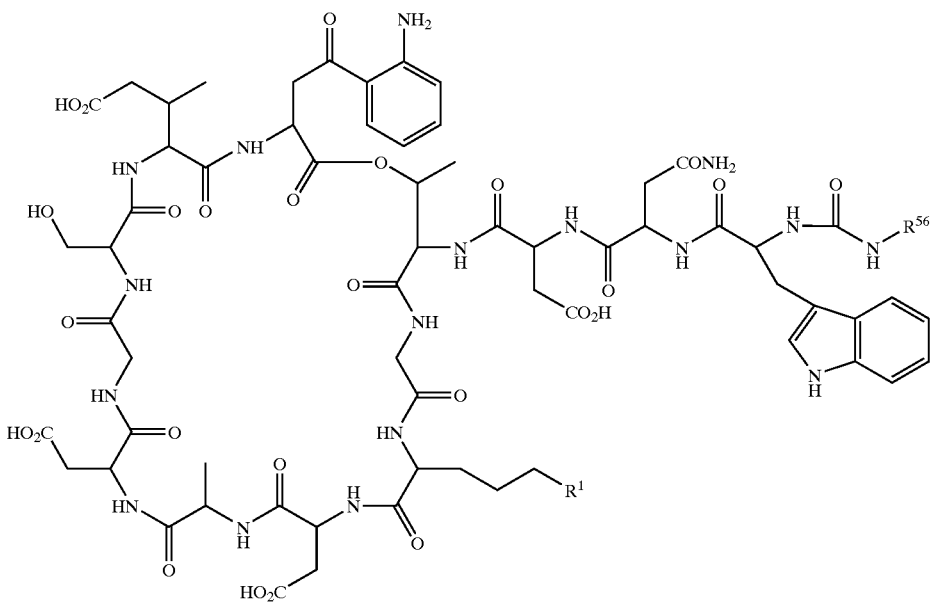

wherein said method comprises treating a compound of claim 23 with a reagent selected from the group consisting of an isocyanates, isothiocyanates, activated esters, acid chlorides, sulfonylchlorides, activated sulfonamides, heterocycles bearing readily displaceable groups, imidates, and lactones; or alternatively, treating a compound of claim 23 reductively with an aldehyde.

25. The compound according to either of claim 1 or 2 wherein said compound is selected from

| Cpd # | R | $R^1$ | $R^2$ |
|---|---|---|---|
| 1 | $NHCONH(CH_2)_7CH_3$ | $NH_2$ | 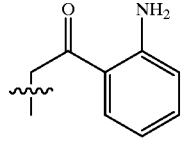 |
| 2 | $NHCONH(CH_2)_{11}CH_3$ | $NH_2$ | 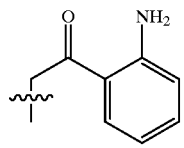 |
| 3 | $NHCONH(CH_2)_{10}CH_3$ | 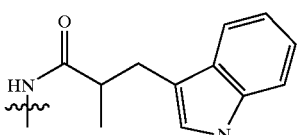 | 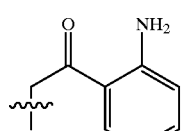 |
| 5 | 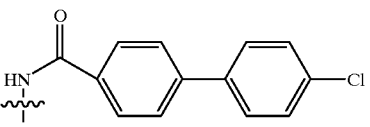 | 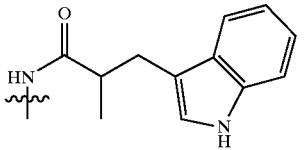 | 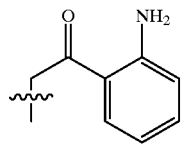 |

-continued
| Cpd # | R | R¹ | R² |
|---|---|---|---|
| 17 | NHCONH(CH₂)₁₁CH₃ | 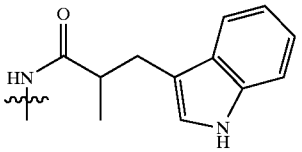 | 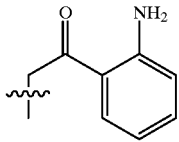 |
| 48 | NHCONH(CH₂)₁₀CH₃ | NH₂ |  |
| 56 | NHCONH(CH₂)₇CH₃ | 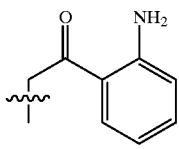 |  |
| 57 | NHCONH(CH₂)₁₀CH₃ | 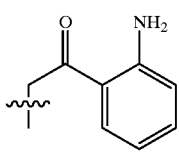 |  |
| 58 | NHCONH(CH₂)₁₁CH₃ | 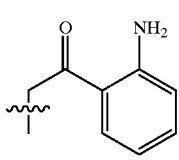 |  |
| 62 | NHCONH(CH₂)₇CH₃ | 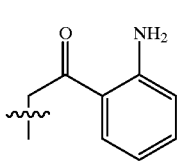 |  |
| 63 | NHCONH(CH₂)₁₀CH₃ | 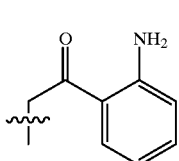 |  |
| 64 | NHCONH(CH₂)₁₁CH₃ | 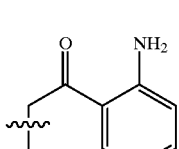 |  |
| 69 | NHCONH(CH₂)₇CH₃ | 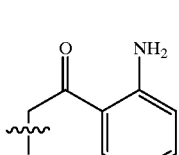 | 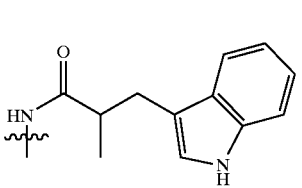 |

-continued

| Cpd # | R | R¹ | R² |
|---|---|---|---|
| 70 | NHCONH(CH$_2$)$_7$CH$_3$ | 2-amino-6-fluorobenzamide linker | 2-aminophenacyl |
| 71 | NHCONH(CH$_2$)$_7$CH$_3$ | guanidine (HN-C(=NH)-NH$_2$) | 2-aminophenacyl |
| 75 | NHCONH(CH$_2$)$_{10}$CH$_3$ | N,N'-di-Boc-guanidine | 2-aminophenacyl |
| 76 | NHCONH(CH$_2$)$_7$CH$_3$ | (5-methoxy-1H-indol-3-yl)methylamino | 2-aminophenacyl |
| 77 | NHCONH(CH$_2$)$_7$CH$_3$ | (1H-imidazol-2-yl)methylamino | 2-aminophenacyl |
| 78 | NHCONH(CH$_2$)$_7$CH$_3$ | (6-nitroquinolin-2-yl)methylamino | 2-aminophenacyl |
| 87 | NHCONH(CH$_2$)$_{11}$CH$_3$ | (5-methoxy-1H-indol-3-yl)methylamino | 2-aminophenacyl |
| 88 | NHCONH(CH$_2$)$_{11}$CH$_3$ | (6-nitroquinolin-2-yl)methylamino | 2-aminophenacyl |
| 89 | NHCONH(CH$_2$)$_{11}$CH$_3$ | (1H-imidazol-2-yl)methylamino | 2-aminophenacyl |

-continued

| Cpd # | R | R¹ | R² |
|---|---|---|---|
| 108 | NHCONH(CH₂)₁₀CH₃ | 2-amino-6-fluorobenzamide (HN-linked) | 2'-aminophenyl ketone |
| 113 | NHCONH(CH₂)₁₀CH₃ | (1H-imidazol-2-yl)methylamino | 2'-aminophenyl ketone |
| 114 | NHCONH(CH₂)₁₀CH₃ | (5-methoxy-1H-indol-3-yl)methylamino | 2'-aminophenyl ketone |
| 117 | NHCONH(CH₂)₈CH₃ | NHBoc | 2'-aminophenyl ketone |
| 118 | NHCONH(CH₂)₈CH₃ | NH₂ | 2'-aminophenyl ketone |
| 119 | NHCONH(CH₂)₉CH₃ | NHBoc | 2'-aminophenyl ketone |
| 120 | NHCONH(CH₂)₉CH₃ | NH₂ | 2'-aminophenyl ketone |

26. The compound according to claim 25 wherein said compound is selected from

| Cpd # | R | R¹ | R² |
|---|---|---|---|
| 2 | NHCONH(CH₂)₁₁CH₃ | NH₂ | 2'-aminophenyl ketone |

| Cpd # | R | R¹ | R² |
|---|---|---|---|
| 3 | NHCONH(CH₂)₁₀CH₃ | ![indole propanamide] | ![2-aminobenzoyl] |
| 48 | NHCONH(CH₂)₁₀CH₃ | NH₂ | ![2-aminobenzoyl] |
| 89 | NHCONH(CH₂)₁₁CH₃ | ![imidazolylmethylamino] | ![2-aminobenzoyl] |
| 118 | NHCONH(CH₂)₈CH₃ | NH₂ | ![2-aminobenzoyl] |
| 120 | NHCONH(CH₂)₉CH₃ | NH₂ | ![2-aminobenzoyl] |

27. The compound according claim 2, wherein R is selected from the group consisting of:

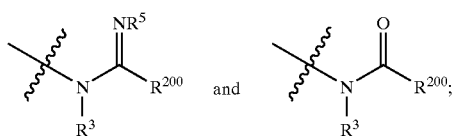

wherein each of $R^3$ and $R^5$ is independently selected from the group consisting of hydrido, alkyl, aryl, heterocyclyl and heteroaryl, and wherein $R^{200}$ is aryl.

28. The compound accordiug to claim 27, wherein R is

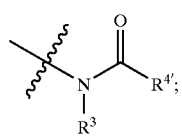

and wherein $R^{4'}$ is a substituted phenyl.

29. The compound according to claim 28, wherein R is

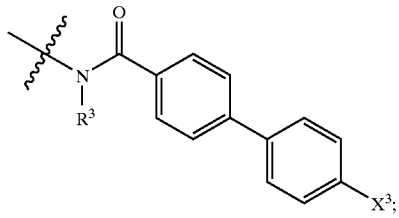

and wherein $X^3$ is chloro or trifluoromethyl.

30. The method according to claim 19, wherein anti-folate agents are sulfonamides.

31. The method according to claim 18, wherein the second antimicrobial agent is a synthetic antibacterial selected from the group consisting of nitrofurans, methenamine mandelate and methenamine hippurate.

* * * * *